(12) United States Patent
Gokel et al.

(10) Patent No.: US 7,129,208 B2
(45) Date of Patent: Oct. 31, 2006

(54) SYNTHETIC ION CHANNELS

(75) Inventors: George W. Gokel, Chesterfield, MO (US); Paul H. Schlesinger, University City, MO (US)

(73) Assignee: Washington University, St. Louis, MO (US)

( * ) Notice: Subject to any disclaimer, the term of this patent is extended or adjusted under 35 U.S.C. 154(b) by 195 days.

(21) Appl. No.: 10/341,960

(22) Filed: Jan. 14, 2003

(65) Prior Publication Data

US 2003/0176641 A1 Sep. 18, 2003

Related U.S. Application Data

(60) Provisional application No. 60/348,803, filed on Jan. 14, 2002.

(51) Int. Cl.
*C08H 1/00* (2006.01)
*A61K 38/10* (2006.01)
*C08G 69/00* (2006.01)

(52) U.S. Cl. .......................... 514/2; 530/300; 530/350; 530/333; 530/402

(58) Field of Classification Search .................... 514/2; 530/300, 350, 333, 402
See application file for complete search history.

(56) References Cited

U.S. PATENT DOCUMENTS

| | | | |
|---|---|---|---|
| 5,204,239 A * | 4/1993 | Gitler et al. ................. | 435/7.1 |
| 5,368,712 A | 11/1994 | Tomich et al. | |
| 5,516,890 A | 5/1996 | Tomich et al. | |
| 5,654,274 A * | 8/1997 | Kari ............................ | 514/12 |
| 6,063,594 A | 5/2000 | Bandman et al. | |
| 6,077,826 A | 6/2000 | Tomich et al. | |
| 6,093,567 A | 7/2000 | Gregory et al. | |
| 6,228,616 B1 | 5/2001 | Bandman et al. | |
| 6,294,350 B1 | 9/2001 | Peterson | |

OTHER PUBLICATIONS

Abel, E. et al., Hydraphile Channels: Structural and Fluorescent Probes of Position and Function in a Phospholipid Bilayer, J. Am. Chem. Soc., (1999), pp. 9043-9052, vol. 121.
Akerfeldt, K.S. et al., Synthetic Peptides as Models for Ion Channel Proteins, Acc. Chem. Res. (1993), pp. 191-197, vol. 26.
Al-Awqati, Q., Chloride Channels of Intracellular Organelles, Current Opinion in Cell Biology, (1995), pp. 504-508, vol. 7.
Brandl, C.J. et al., Hypothesis About the Function of Membrane-Buried Proline Residues in Transport Proteins, Proc. Natl. Acad. Sci., (1986), pp. 917-921, vol. 83.
Clark, T.D. et al., Self-Assembling Cyclin β-Peptide Nanotubes as Artificial Transmembrane Ion Channels, J. Am. Chem. Soc., (1998), pp. 651-656, vol. 120.
Corringer, P-J et al., Mutational Analysis of the Charge Selectivity Filter of the α7 Nicotinic Acetylcholine Receptor, Neuron, (1999), pp. 831-843, vol. 22.
Das, S. et al., Proof for a Nonproteinaceous Calcium-Selective Channel in *Escherichia coli* by Total Synthesis from (R)-3-Hydroxybutanoic Acid and Inorganic Polyphosphate, Proc. Natl. Acd. Sci., (1997), pp. 9075-9079, vol. 94.
Dutzler, R. et al., X-ray Structure of a ClC Chloride Channel at 3.0 Å Reveals the Molecular Basis of Anion Selectivity, Nature, (2002), pp. 287-294, vol. 415.
Fahlke, C. et al., Pore-Forming Segments in Voltage-Gated Chloride Channels, Nature, (1997), pp. 529-532, vol. 390.
Fahlke, C. et al., Residues Lining the Inner Pore Vestibule of Human Muscle Chloride Channels, The Journal of Biological Chemistry, (2001), pp. 1759-1765, vol. 276:3.
Frizzell R.A. et al., Altered Regulation of Airway Epithelial Cell Chloride Channels in Cystic Fibrosis, Science, (1986), pp. 558-560, vol. 233.
Fyles, T.M. et al., Ion Channel Models, Comprehensive Supramol. Chem., (1996), pp. 53-77, vol. 10.
Galzi, J-L. et al., Mutations in the Channel Domain of a Neuronal Nicotinic Receptor Convert Ion Selectivity from Cationic to Anionic, Nature, (1992), pp. 500-505, vol. 359.
Gibbs, N. et al., Helix Bending in Alamethicin: Molecular Dynamics Simulations and Amide Hydrogen Exchange in Methanol, Biophysical Journal, (1997), pp. 2490-2495, vol. 72.
Gokel, G.W., Hydraphiles: Design, Synthesis and Analysis of a Family of Synthetic, Cation-Conducting Channels, Chem. Commun., (2000), pp. 1-9.
Gokel, G.W. et al., Synthetic Models of Cation-Conducting Channels, Chem. soc. Rev., (2001, pp 274-286, vol. 30.
Gokel, G.W. et al., Synthetic Organic Chemical Models for Transmembrane Channels, Acc. Chem. Res., (1996), pp. 425-432, vol. 29.
Hille, B., Pharmacological Modifications of the Sodium Channels of Frog Nerve, The Journal of General Physiology, (1968), pp. 199-219, vol. 51.
Hwang, T-C et al., Cl Channels in CF: Lack of Activation by Protein Kinase C and cAMP-Dependent Protein Kinase, Science, (1989), pp. 1351-1353, vol. 244.

(Continued)

*Primary Examiner*—Jon Weber
*Assistant Examiner*—Samuel W. Liu
(74) *Attorney, Agent, or Firm*—Senniger Powers

(57) ABSTRACT

The present invention relates to amphiphiles for the formation of a synthetic ion channel in a phospholipid bilayer or biomembrane. The synthetic channel selectively transports chloride ions across the phospholipid bilayer or the membrane. Said amphiphiles impart ion permeability to the phospholipid bilayers or biomembrane and also modulate cellular volume in mammalian cells in vitro.

28 Claims, 8 Drawing Sheets

OTHER PUBLICATIONS

Hyde, S.C. et al., Structural Model of ATP-Binding Proteins Associated with Cystic Fibrosis, Multidrug Resistance and Bacterial Transport, Nature, (1990), pp. 362-365, vol. 346.

Ido, Y. et al., Prevention of Vascular and Neural Dysfunction in Diabetic Rats by C-Peptide, Science, (1997), pp. 563-566, vol. 277.

Jullien, L. et al., The "CHUNDLE" Approach to Molecular Channels Synthesis of a Macrocycle-Based Molecular Bundle, Tetrahedron Letters, (1988), pp. 3803-3806, vol. 29:31.

Lear, J.D. et al., Synthetic Amphiphilic Peptide Models for Protein Ion Channels, Research Articles, (1988), 1177-1181, vol. 240.

Levitt, D.G., Kinetics of Movement in Narrow Channels, Current Topics in Membranes and Transport, (1984), pp. 181-197, vol. 21.

Li, M. et al., Cyclic AMP-Dependent Protein Kinase Opens Chloride Channels in Normal but no Cystic Fibrosis Airway Epithelium, Nature, (1988), pp. 358-360, vol. 331.

Merlin, D. et al., Cryptdin-3 Induces Novel Apical Conductance(s) in C1 Secretory, Including Cystic Fibrosis, Epithelia, Am J Physiol Cell Physiol, pp. C296-C302, vol. 280.

Miller, C., Ion Channels: Doing Hard Chemistry with Hard Ions, Current Opinion in Chemical Biology, (2000, pp. 148-151, vol. 4.

Montal, M., Design of Molecular Function: Channels of Communication, Annu. Rev. Biophys. Biomol. Struct., (1995), pp. 31-57, vol. 24.

Mutter, M. et al., Strategies for the De Novo Design of Proteins, Tetrahedron, (1988), pp. 771-785, vol. 44:3.

Oiki, S. et al., Channel Protein Engineering: Synthetic 22-mer Peptide from the Primary Structure of the Voltage-Sensitive Sodium Channel Forms Ionic Channels in Lipid Bilayers, Proc. Natl. Acad. Sci., (1988), pp. 2393-2397, vol. 85.

Reusch, R.N., Ion Recognition and Transport by Poly-($R$)-3-Hydroxybutyrates and Inorganic Polyphosphates, Advances in Supramolecular Chemistry, pp. 49-98, vol. 7.

Rex, S. et al., Quantitative Studies on the Melittin-Induced Leakage Mechanism of Lipid Vesicles, Biochemistry, (1998), pp. 2336-2345, vol. 37.

Riordan, J.R. et al., Identification of the Cystic Fibrosis Gene: Cloning and Characterization of Complementary DNA, Science, (1989), pp. 1066-1073, vol. 245.

Rommens, J.M. et al., Identification of the Cystic Fibrosis Gene: Chromosome Walking and Jumping, Research Articles, (1989), pp. 1059-1065, vol. 245.

Saito, M. et al., BAX-Dependent Transport of Cytochrome C Reconstituted in Pure Liposomes, Nature Cell Biology, (2000), pp. 553-555, vol. 2.

Schlesinger, P.H. et al., Comparison of the Ion Channel Characteristics of Proapoptotic BAX and Antiapoptotic BCL-2, Proc. Natl. Acad. Sci., (1997), pp. 11357-11362, vol. 94.

Schlesinger, P.H., Measuring the pH of Pathogen-Containing Phagosomes, Methods in Cell Biology, pp. 289-311, vol. 45.

Starostin, A.V. et al., An Anion-Selective Analogue of the Channel-Forming Peptide Alamethicin, Biochemistry, (1999), pp. 6144-6150, vol. 38.

Steinmeyer, K. et al., Primary Structure and Functional Expression of a Developmentally Regulated Skeletal Muscle Chloride Channel, Nature, (1991), pp. 301-304, vol. 354.

Szoka, F., Jr. et al., Procedure for Preparation of Liposomes with Large Internal Aqueous Space and High Capture by Reverse-Phase Evaporation, Proc. Natl. Acad. Sci., (1978), pp. 4194-4198, vol. 75:9.

Tieleman, D.P. et al., Alamethicin Helices in a Bilayer and in Solution: Molecular Dynamics Simulations, Biophysical Journal, (1999), pp. 40-49, vol. 76.

Voyer, N. et al., A Novel Functional Artificial Ion Channel, J. Am. Chem. Soc., (1995), pp. 6599-6600, vol. 117.

Voyer, N. et al., Electrical Activity of Artificial Ion Channels Incorporated into Planar Lipid Bilayers, J. Chem. Soc., Perkin Trans, (1997), pp. 1469-1471, vol. 2.

Wagner, H. et al., Oligo-THF Peptides: Synthesis, Membrane Insertion, and Studies of Ion Channel Activity, Angew. Chem. Int. Ed. Engl., (1996), pp. 2643-2646, vol. 35:22.

Welsh, M.J., An Apical-Membrane Chloride Channel in Human Tracheal Epithelium, Science, pp. 1648-1650, vol. 232.

Welsh, M.J. et al., Chloride and Potassium Channels in Cystic Fibrosis Airway Epithelia, Nature, (1986), pp. 467-470, vol. 322.

Yang, L. et al., Barrel-Stave Model or Toroidal Model? A Case Study on Melittin Pores, Biophysical Journal, (2001), pp. 1475-1485, vol. 81.

Schlesinger et al. "A Hydrocarbon Anchored Peptide that Forms a Chloride-Selective Channel in Liposomes" Chem. Commun., vol. 8 (2002) pp. 840-841.

Yang et al. "Cyclic Hexapeptide of D,L-α-Aminoxy Acids as a Selective Receptor for Chloride Ion" JACS, vol. 124, No. 42 (2002) pp. 12410-12411.

Lanigan et al. "Designed Peptide Analogues of the Postassium Channel Blocker ShK Toxin" Biochemistry, vol. 40, No. 51 (2001) pp. 15528-15537.

Schlesinger et al. "SCMTR—A Chloride-Selective, Membrane-Anchored Peptide Channel that Exhibits Voltage Gating" JACS, vol. 124, No. 9 (2002) pp. 1848-1849.

International Search Report from analogous application PCT/US03/00973 dated Aug. 14, 2003.

* cited by examiner

[CH₃(CH₂)₁₇]₂NCOCH₂OCH₂CO-GGGPGGG-OCH₂Ph

SEQUENCE LISTING

```
<160> NUMBER OF SEQ ID NOS: 7
<210> SEQ ID NO 1
<211> LENGTH: 4
<212> TYPE: PRT
<213> ORGANISM: Artificial Sequence
<220> FEATURE:
<223> OTHER INFORMATION: Synthetic amino acids

<400> SEQUENCE: 1

Pro Gly Gly Gly
1

<210> SEQ ID NO 2
<211> LENGTH: 7
<212> TYPE: PRT
<213> ORGANISM: Artificial Sequence
<220> FEATURE:
<223> OTHER INFORMATION: Synthetic amino acids

<400> SEQUENCE: 2

Gly Gly Gly Pro Gly Gly Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic amino acids

<400> SEQUENCE: 3

Gly Gly Gly Leu Gly Gly Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic amino acids
<220> FEATURE:
<221> NAME/KEY: MISC_FEATURE
<222> LOCATION: (1)..(1)
<223> OTHER INFORMATION: Xaa = pipecolic acid (PIP)

<400> SEQUENCE: 4

Xaa Gly Gly Gly
1

<210> SEQ ID NO 5
<211> LENGTH: 7
<212> TYPE: PRT
<213> ORGANISM: Artificial Sequence
<220> FEATURE:
<223> OTHER INFORMATION: Synthetic amino acids
<220> FEATURE:
<221> NAME/KEY: MISC_FEATURE
<222> LOCATION: (4)..(4)
<223> OTHER INFORMATION: Xaa = pipecolic acid (PIP)
```

```
<400> SEQUENCE: 5

Gly Gly Gly Xaa Gly Gly Gly
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic amino acids
<220> FEATURE:
<221> NAME/KEY: MISC_FEATURE
<222> LOCATION: (1)..(1)
<223> OTHER INFORMATION: Xaa = 3-Amino-4-methoxybenzoic acid

<400> SEQUENCE: 6

Xaa Gly Gly Gly
1

<210> SEQ ID NO 7
<211> LENGTH: 7
<212> TYPE: PRT
<213> ORGANISM: Artificial Sequence
<220> FEATURE:
<223> OTHER INFORMATION: Synthetic amino acids
<220> FEATURE:
<221> NAME/KEY: MISC_FEATURE
<222> LOCATION: (4)..(4)
<223> OTHER INFORMATION: Xaa = 3-amino-4-methoxybenzoic acid

<400> SEQUENCE: 7

Gly Gly Gly Xaa Gly Gly Gly
1               5
```

SYNTHETIC ION CHANNELS

REFERENCE TO RELATED APPLICATIONS

This application claims the benefit of U.S. Provisional Application No. 60/348,803 filed Jan. 14, 2002, the entire contents of which are incorporated herein by reference.

This invention was made with Government support under NIH Grant #GM 36262 awarded by the National Institutes of Health. The Government has certain rights in the invention.

FIELD OF THE INVENTION

This invention relates to biological membranes incorporating synthetic ion channels, ion channel forming compositions, and methods for the formation of ion channels in biological and synthetic membranes and for their use. In one embodiment, the synthetic channel selectively transports chloride ions across a membrane.

BACKGROUND OF THE INVENTION

Ion channels in mammalian systems are the subject of intensive scientific investigation because of the importance and the variety of their functions.[1] Such channels are located in the phospholipid bilayer membranes of cells and permit the transport at a high rate of a particular cation or anion. Natural ion channels are generally understood to be polypeptide or protein structures. These large molecules form pores within membranes that provide diffusion pathways for ionic species that are exquisitely controlled and specific. These diffusion pathways control the movement of ion currents in membranes generating membrane potentials and currents that influence all aspects of cellular physiology. Channel proteins have "open" and "closed" states that are sensitive to membrane potential (voltage gating) or to the presence or absence of regulatory molecules (ligand gating).[2] The channel molecules typically exhibit selectivity for one particular cation or anion, in vivo. Often, they can permit the selected ion to be transported preferentially in one direction (rectification). In combination, these characteristics allow ion channels to provide the rapid and integrated control of cellular activity required for mammalian function.

The functions of ion channel proteins have generally been studied by using proteins reconstituted from natural sources or expressed by cloning techniques. The proteins thus obtained are then studied for ion conduction in a lipid bilayer membrane. The lipid bilayer prevents ion diffusion except through the channel and allows detailed study of the currents that result. In this configuration, picoAmp currents can be studied allowing characterization of single channel molecules. Using these methods, it is possible to determine channel conductance, ion selectivity, gating kinetics and to study modulation of channel activity. Using these techniques, the characteristics of many different ion channels have been determined showing a diversity of properties that includes cation and anion specific channels for both monovalent and polyvalent ions.

A common failing of existing synthetic channels is their inability to provide the degree of mimetic fidelity to native channels that would permit meaningful use of the synthesized versions in biomedical applications.[3-5] The peptide ion channels produced by the synthetic approach of Lear et al.[4] were not intended to be mimetic, but were simply designed to show ion transport. These compounds were formed from repeating units involving only leucine and serine. Mutter et al. have suggested that synthetic channel peptides may be made by linking amphipathic α-helix and β-sheet peptides to a synthetic peptide template.[6] The compounds of Mutter et al. were less selective and efficient than their natural channel counterparts.

During the past two decades, numerous attempts have been made to develop synthetic ion channels. These include the total synthesis of a simple but natural channel,[7] non-naturally occurring peptide aggregates,[8] cyclic peptide nanotubes,[9] hybrid crown ether-peptide structures,[10] oligomeric structures,[11] and completely synthetic compounds called "hydraphiles."[12] Other synthetic channel structures that have been assessed for their ability to transport cations may be identified from recent reviews on the subject.[13] Fewer attempts have been reported to develop anion channels.[14]

The discovery of functional synthetic ion channels would provide a means to investigate and modulate the regulation of membrane potentials, intracellular pH, cell volume, signal transduction, and transepithelial ion transport in tissues containing absorptive or secretory epithelia under normal and disease conditions. Discovery of novel synthetic ion channel compounds satisfies a need in the art by providing new compositions useful in conditions and diseases wherein transport of ions plays a role.

Such channel assemblies can be used, e.g., in the treatment of diseases such as cystic fibrosis (CF) and adult polycystic kidney disease (APKD). Cystic Fibrosis (CF) is the most common fatal genetic disease in Caucasians.[15] Approximately one in every 2,500 Americans of European descent is born with the disease. Despite current standard therapy, the median age of survival is only 26 years. Disease of the pulmonary airways is the major cause of morbidity and is responsible for 95% of the mortality.

Based on both genetic and molecular analyses, a gene associated with CF was isolated as part of 21 individual cDNA clones and its protein product predicted.[16-18] The protein product of the CF associated gene is called the cystic fibrosis transmembrane conductance regulator (CFTR).[17] CFTR is a protein of approximately 1480 amino acids made up of two repeated elements, each comprising six transmembrane segments and a nucleotide binding domain. The two repeats are separated by a large, polar, so-called R-domain containing nucleotide binding sites and multiple potential phosphorylation sites. Based on its predicted domain structure, CFTR is a member of a class of related proteins that includes the multi drug resistance (MDR) or P-glycoprotein, bovine adenyl cyclase, the yeast STE6 protein and several bacterial amino acid transport proteins.[17,19] Proteins in this group, characteristically, are involved in the transport of molecules into or out of cells.

CFTR has been postulated to regulate the outward flow of anions from epithelial cells in response to phosphorylation by cyclic AMP-dependent protein kinase or protein kinase C.[17,20-24] Hence, for CF and other conditions, the development of synthetic anion channels has significant utility in terms of investigating cellular anion imbalances and in modulating such conditions.

Intracellular compartments are critical to the organization of eukaryotic cells. The vast majority of these compartments are used in the intracellular transport of macromolecules to locations within the cell or in the uptake and processing of extracellular objects. These compartments include the endocytic vesicles, secretory vesicles, phagosomal vesicles and lysosomes primarily but also include a number of associated specialized vesicles. These vesicles have in common the ability to acidify and then employ this acidic pH in their required functions.[25] The acidification of these vesicles critically depends upon the chloride permeability of their limiting bilayer membrane. Because they insert into bilayer membranes at low concentrations, in one embodiment, applicants' chloride channel assemblies can be used to study the precise role of chloride permeability in the functions of these vesicles. In addition, the modification of these functions will have key influences upon the secretion, uptake and processing of proteins, bacteria and viruses by eukaryotic cells. Specialized cells such as osteoclasts and renal tubular cells use chloride dependent acidification for bone metabolism and critical detoxification activities.

SUMMARY OF THE INVENTION

Among the various aspects of the present invention is the provision of ion channel forming compositions, biological membranes having synthetic ion channels, and methods for the formation of the synthetic ion channels in biological membranes and for their use.

One aspect of the present invention is an amphiphile for the formation of a synthetic ion channel in a phospholipid bilayer membrane. The amphiphile corresponds to the formula $$A\text{-}C\text{-}H^1\text{-}B\text{-}H^2\text{-}T$$

wherein

A is hydrocarbyl, substituted hydrocarbyl, heterocyclo or amino optionally linked to the connector, C, through a nitrogen, oxygen or sulfur atom;

C is a single covalent bond or a moiety comprising hydrocarbyl, substituted hydrocarbyl or heterocyclo;

$H^1$ is substituted hydrocarbyl or heterocyclo and, in combination with other units of the amphiphile functions as a head group for the amphiphile;

B is a substituted hydrocarbyl, carbocyclic or heterocyclic unit;

$H^2$ is substituted hydrocarbyl or heterocyclo and, in combination with other units of the amphiphile functions as a headgroup for the amphiphile; and T is hydrocarbyl, substituted hydrocarbyl or heterocyclo.

Another aspect of the present invention is a combination, the combination comprising a phospholipid bilayer membrane and an assembly of synthetic amphiphiles wherein the assembly forms an ion channel through the membrane.

Another aspect of the present invention is a process for forming a synthetic ion channel in a phospholipid bilayer membrane, the process comprising combining the membrane with synthetic amphiphiles having the capacity to self-assemble to form the ion channel.

A further aspect of the present invention is a process for modulating the flow of ions through a phospholipid bilayer membrane, the process comprising forming an ion channel in the membrane from an assembly of synthetic amphiphiles and thereafter imposing an ion gradient or a membrane potential.

Other aspects of the present invention will be in part apparent and in part pointed out hereinafter.

The anchor-connector was designed to mimic a phospholipid monomer in size, polarity, and functional group position. In it, anchor and phosphatidylethanolamine monomers are compared. Note that in this illustration, the alkyl groups are hexadecyl, $CH_3(CH_2)_{15}$. The synthesis of this exemplary anchor-connector unit is described in Example 1.

Figure 1:
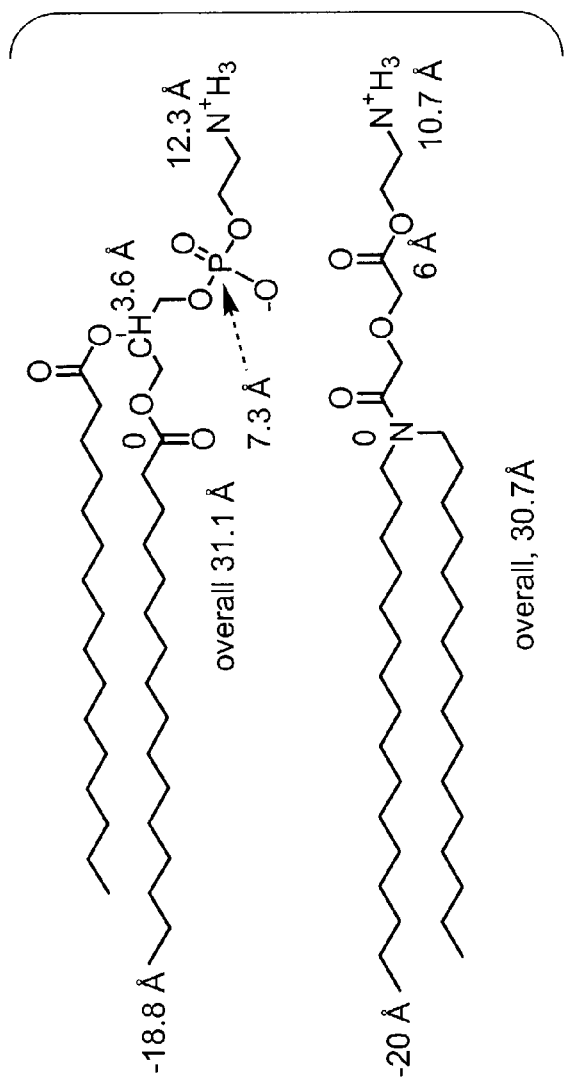
FIG. 1—Anchor-connector chemical structure.
Figure 2:
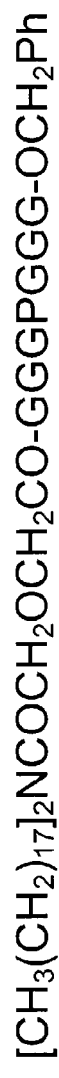

FIG. 2—$(C_{18}H_{37})_2NCOCH_2OCH_2CO$-Gly-Gly-Gly-Pro-Gly-Gly-Gly-$OCH_2Ph$ (SEQ ID NO.: 2) chemical structure. The synthesis of this amphiphile depicted, exemplary of the present invention, is described in Example 2.

Figure 3:
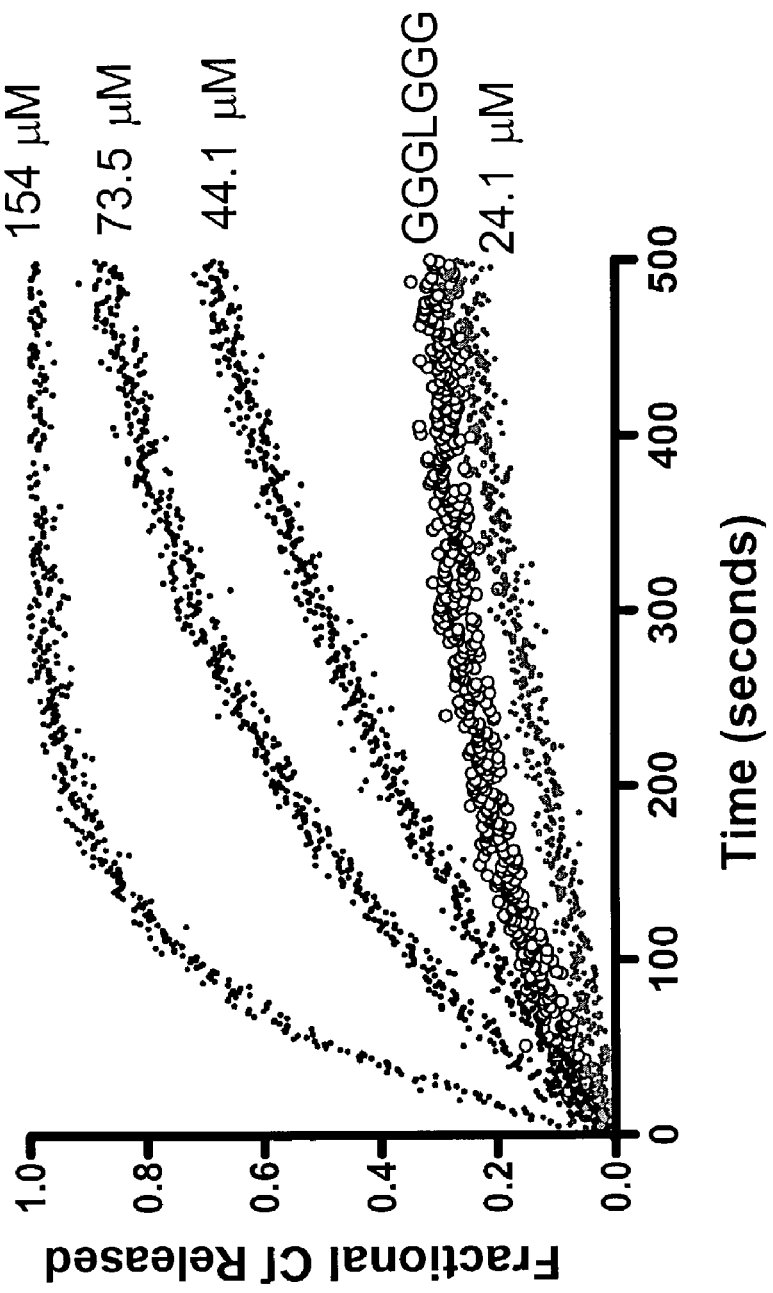

FIG. 3—Measurement of chloride release from liposomes containing the amphiphile $(C_{18}H_{37})_2NCOCH_2OCH_2CO$-Gly-Gly-Gly-Pro-Gly-Gly-Gly-$OCH_2Ph$ (SEQ ID NO.: 2). This experimental result is described in detail in Example 20.

Figure 4:
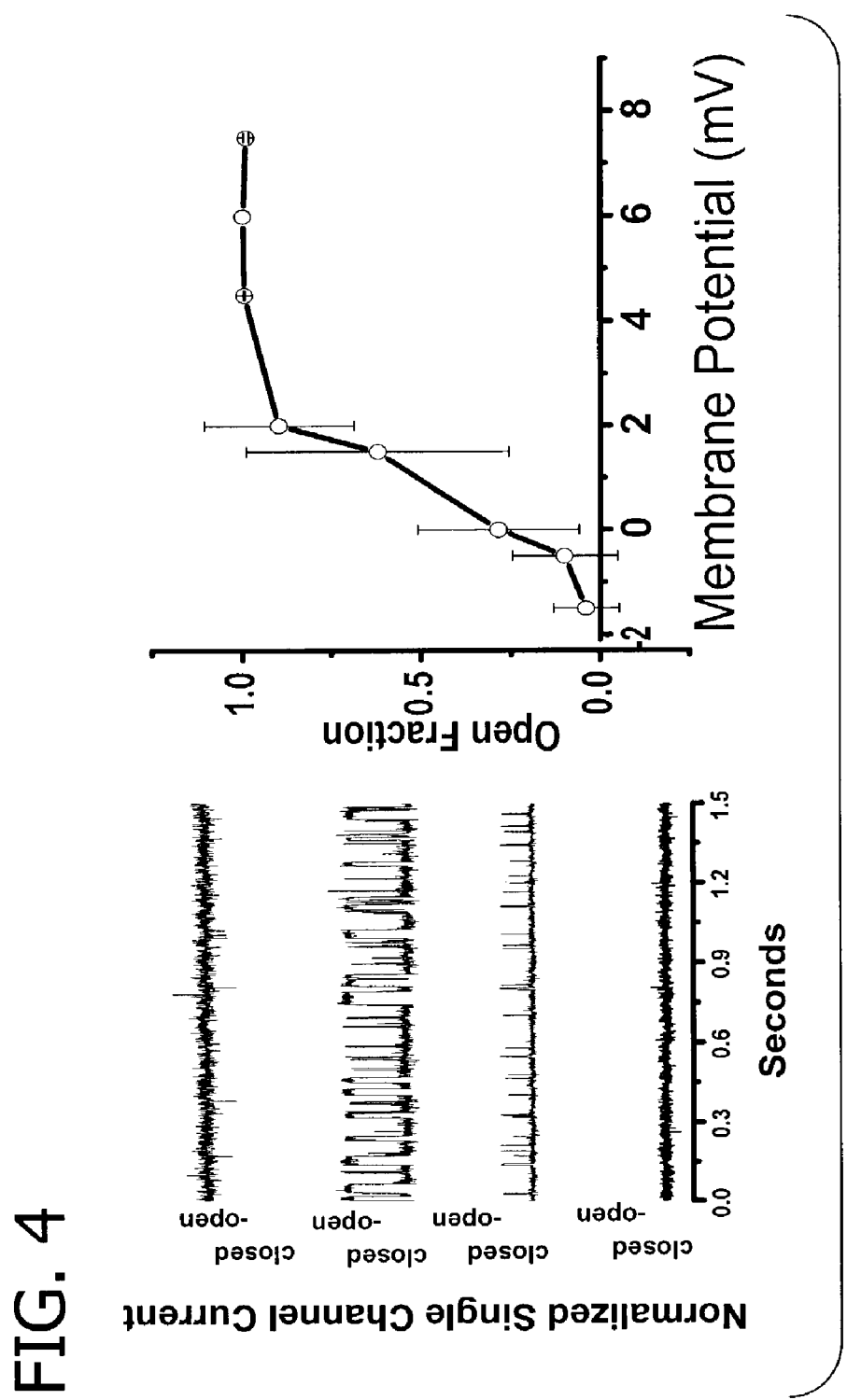

FIG. 4—The amphiphile $(C_{18}H_{37})_2NCOCH_2OCH_2CO$-Gly-Gly-Gly-Pro-Gly-Gly-Gly-$OCH_2Ph$ (SEQ ID NO.: 2) exhibits voltage-dependent gating. This experimental result is described in detail in Example 21.

Figure 5:
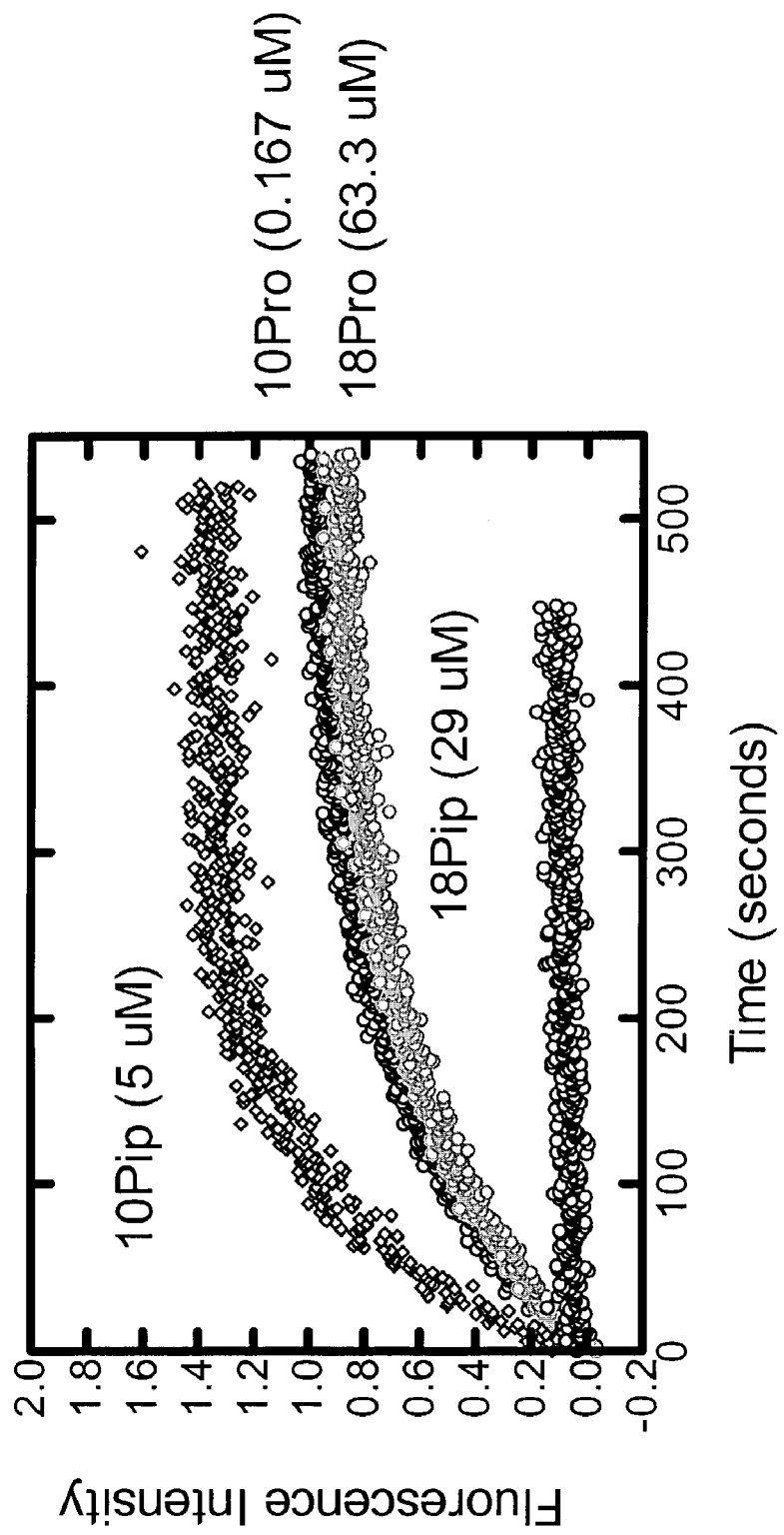

FIG. 5—Graph illustrating the release of carboxyfluorescein from phospholipid liposomes mediated by $(H_{21}C_{10})_2$ $NCOCH_2OCH_2CON$-Gly-Gly-Gly-Pip-Gly-Gly-Gly-$OCH_2Ph$ (10Pip) (SEQ ID NO.: 5), $(H_{21}C_{10})_2$ $NCOCH_2OCH_2CON$-Gly-Gly-Gly-Pro-Gly-Gly-Gly-$OCH_2Ph$ (10Pro) (SEQ ID NO.: 2), $(H_{37}C_{18})_2$ $NCOCH_2OCH_2CON$-Gly-Gly-Gly-Pip-Gly-Gly-Gly-$OCH_2Ph$ (18Pip) (SEQ ID NO.: 5), and $(H_{37}C_{18})_2$ $NCOCH_2OCH_2CON$-Gly-Gly-Gly-Pro-Gly-Gly-Gly-$OCH_2Ph$ (18Pro) (SEQ ID NO.: 2). Transport was assessed by fluorescence measurements as described in detail in Example 20.

Figure 6:
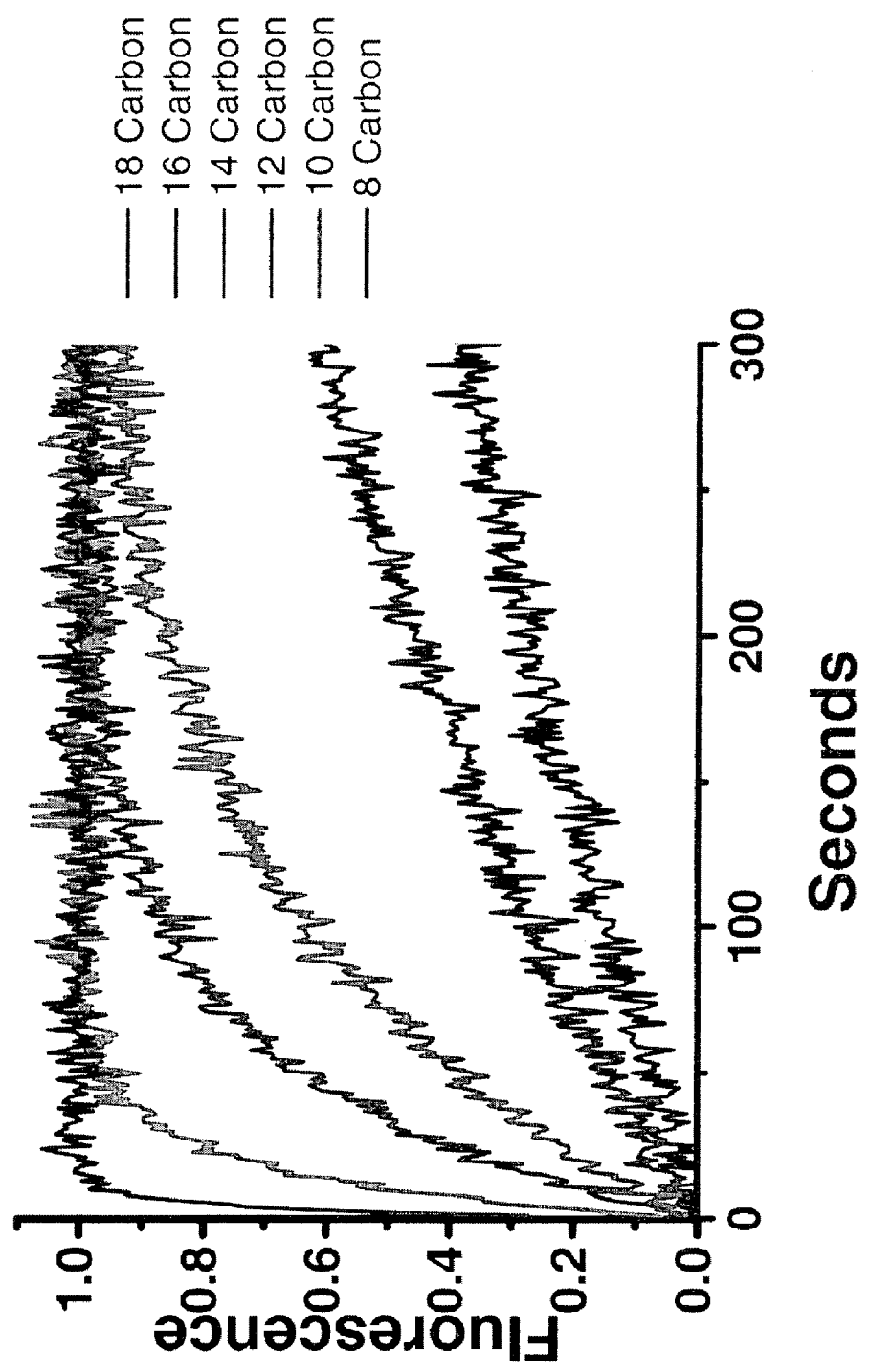

FIG. 6—Graph illustrating the release of carboxyfluorescein from phospholipid liposomes mediated by $(H_{17}C_8)_2$ $NCOCH_2OCH_2CON$-Gly-Gly-Gly-Pro-Gly-Gly-Gly-$OCH_2Ph$ (SEQ ID NO.: 2), $(H_{21}C_{10})_2NCOCH_2OCH_2CON$-Gly-Gly-Gly-Pro-Gly-Gly-Gly-$OCH_2Ph$ (SEQ ID NO.: 2), 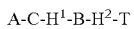$NCOCH_2$ $OCH_2CON$-Gly-Gly-Gly-Pro-Gly-Gly-Gly-$OCH_2Ph$ (SEQ ID NO.: 2), $(H_{29}C_{14})_2$ $NCOCH_2OCH_2CON$-Gly-Gly-Gly-Pro-Gly-Gly-Gly-$OCH_2Ph$ (SEQ ID NO.: 2), $(H_{33}C_{16})_2NCOCH_2OCH_2CON$-Gly-Gly-Gly-Pro-Gly-Gly-Gly-$OCH_2Ph$ (SEQ ID NO.: 2), and $(H_{37}C_{18})2NCOCH_2OCH_2CON$-Gly-Gly-Gly-Pro-Gly-Gly-Gly-$OCH_2Ph$ (SEQ ID NO.: 2). Transport was assessed by fluorescence measurements as described in detail Example 20.

Figure 7A:
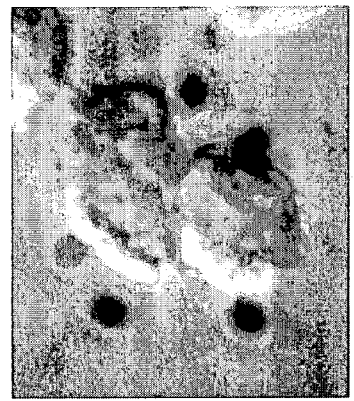
Figure 7B:
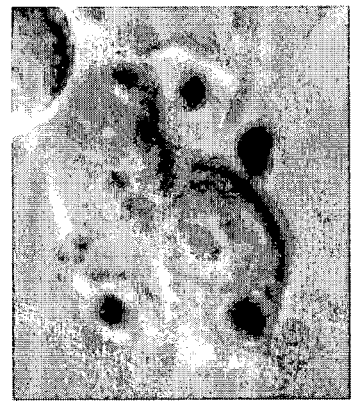
Figure 7B:
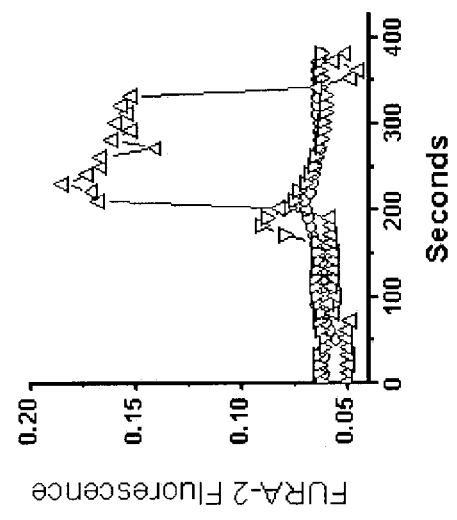
Figure 7C:
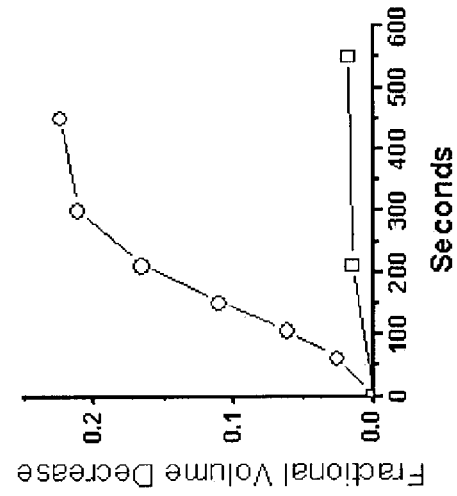

FIG. 7A–C—Illustrates the effect of the amphiphile $(C_{18}H_{37})_2NCOCH_2OCH_2CO$-Gly-Gly-Gly-Pro-Gly-Gly-Gly-$OCH_2Ph$ (SEQ ID NO.: 2) on volume regulation in a monocytic cell line. This experimental result is described in detail in Example 22.

FIG. 8A–D—Illustrates the chloride selectivity of $(C_{18}H_{37})_2NCOCH_2OCH_2CO$-Gly-Gly-Gly-Pro-Gly-Gly-Gly-$OCH_2Ph$ (SEQ ID NO.: 2) as assessed by voltage clamp methods in planar lipid bilayers This experimental result is described in detail in Example 23.

FIG. 9A–E—Illustrates the use of fluorescence dequenching as a method to study pore activation and size of the pore formed by $(C_{18}H_{37})_2NCOCH_2OCH_2CO$-Gly-Gly-Gly-Pro-Gly-Gly-Gly-$OCH_2Ph$ (SEQ ID NO.: 2). This experimental result is described in detail in Example 24.

DETAILED DESCRIPTION OF THE PREFERRED EMBODIMENTS

In biological systems, the composition of a functional membrane varies depending upon its location. For example, a plasma membrane may be approximately 50% by weight protein, have a capacitance of 1 microfarad per square micron and a leak conductance of 0.2–1 picoamp per micron; a mitochondrial membrane may be more than 70% protein, have no measurable leak conductance and areas of membrane that are devoid of protein but have 5–10% arachidonic acids with K+ permeabilities of hundreds of picoamps per square micron. In addition, a pure phosphatidylcholine membrane has almost no conductance. Each of these membranes, however, regardless of the extent of protein content comprises a phospholipid bilayer. One aspect of the present invention, therefore, is the formation of synthetic channels in a phospholipid bilayer whether the phospholipid bilayer is of natural or synthetic origin.

Significantly, the amphiphiles of the present invention have the ability to self-assemble in physiological and non-physiological systems and form ion channels in phospholipid bilayer membranes. By varying the size and composition of the amphiphile as described herein, in one embodiment ion channels having pore sizes (i.e., effective diameter) of about 4 to about 25 Å may be assembled; in another embodiment, ion channels having pore sizes (i.e., effective diameter) of about 6 to about 20 Å may be assembled. Advantageously, these amphiphiles and the channels formed by the assembly thereof in a phospholipid bilayer offer a wide range of investigational and treatment applications.

In one embodiment, the amphiphiles of the present invention are assembled to form anion channels. For example, the amphiphiles may assemble to form a channel for chloride, nitrate, sulfate, bicarbonate, phosphate, acetate or carboxyfluorescein anions in phospholipid bilayers. In another embodiment, the amphiphiles are assembled to form cation channels. For example, the amphiphiles may assemble to form a channel that conducts sodium, potassium, calcium, magnesium, or barium ions in phospholipid bilayers. In addition, the channels may be selective for certain ions. For example, chloride anion over fluoride anion, chloride anion over sulfate anion, chloride anion over sodium cation, or chloride anion over potassium cation.

In general, the amphiphiles of the present invention correspond to formula I:

$$A\text{-}C\text{-}H^1\text{-}B\text{-}H^2\text{-}T \qquad \text{(Formula I)}$$

wherein

A is an anchor unit for embedding the amphiphile in the membrane;

C is a connector unit for joining the anchor unit to other units of the amphiphile;

$H^1$ is a first headgroup unit which, in combination with other units of the amphiphile, defines the channel pore;

B is a unit of the amphiphile that is capable of imparting what may be referred to as a bend, kink, or vertex in the channel pore;

$H^2$ is a second headgroup unit which, in combination with other units of the amphiphile, defines the channel pore; and T is a terminal group of the amphiphile.

The amphiphiles contain a headgroup and a tail with the headgroup providing sufficient polarity and the tail being sufficiently non-polar to characterize the compound as an amphiphile. In general, the anchor unit, A, constitutes at least a portion of the non-polar fraction of the molecule whereas the headgroup units, $H^1$ and $H^2$, and the B unit constitute a portion of the more polar fraction of the molecule. In concert, these regions of the molecule provide it with amphiphilic characteristics, i.e., surface activity or the ability to form aggregates. The former may be tested by surface tension measurements and the latter by light scattering methods that are known to those of ordinary skill in the art.

As noted, the anchor unit, A, at least in part, provides a means for the amphiphile to be embedded in the phospholipid bilayer. Accordingly, the anchor unit is preferably of a shape that promotes retention of the amphiphile within the bilayer. In general, less bulky units are preferred over more bulky units. Thus, for example, linear alkyl moieties such as $CH_3(CH_2)_7$— would typically be preferred over branched alkyl moieties such as $(CH_3)_3CC(CH_3)_2CH_2$— even though the two have the same number of carbon atoms.

In addition, the anchor unit, A, also preferably exhibits sufficient hydrophobicity to promote retention of the amphiphile within the bilayer. In one embodiment, the anchor unit, A, by reference to a partition constant (expressed as log P) between water and n-octanol exhibits a hydrophobicity value of at least 4 (expressed as a decadic logarithm); in another embodiment, the anchor unit, A, contributes sufficient hydrophobicity to the amphiphile such that the hydrophobicity value of the entire amphiphile is at least 2 (expressed as a decadic logarithm).

Anchor units, A, satisfying these shape and hydrophobicity considerations may be selected from a variety of organic units. For example, A may be hydrocarbyl, substituted hydrocarbyl, heterocyclo or amino; optionally, A may be linked to the connector, C, through a nitrogen, oxygen or sulfur atom. Typically, A will be hydrocarbyl, substituted hydrocarbyl or amino. In one embodiment, A is alkyl or substituted alkyl. In another embodiment, A is $C_{16}$ to $C_{50}$ alkyl substituted alkyl with the alkyl substituents being selected from the group consisting of lower alkyl groups having 1–5 carbon atoms. In another embodiment, A is —NR$^1$R$^2$ wherein each of R$^1$ and R$^2$ are independently hydrocarbyl or substituted hydrocarbyl. In yet another embodiment, A is —NR$^1$R$^2$ wherein each of R$^1$ and R$^2$ are independently alkyl or substituted alkyl. Exemplary anchor units include N-methyl-N-hexadecyl, N-ethyl-N-pentadecyl, N,N-didodecyl, N,N-dioctadecyl, and n-octadecyloxy.

The connector, C, is a connector unit that serves to join the anchor unit, A, to the remainder of the amphiphile. In one embodiment, C is a single covalent bond. In another embodiment, C is a moiety having a length and polarity that mimics the size and polarity of the midpolar regime of a phospholipid unit of a bilayer; for example, the connector may have an extended length in the range of about 3 to about 10 Angstroms (A). The presence of ether, thioether, carbonyl, thiocarbonyl, and other polar residues within the connector unit are contemplated. In addition, flexible organic moieties tend to be preferred over more rigid (e.g., cyclic) moieties. If other than a covalent bond, connectors satisfying these design considerations may be selected from a variety of organic units. For example, C may be hydrocarbyl, substituted hydrocarbyl, or heterocyclo. Typically, C will be substituted hydrocarbyl. In one embodiment, C is 1,4-butylene or 1,3-propyleneoxy. Carbonyl groups and common heteroatoms such as nitrogen, oxygen, and sulfur, as substituents or as chain atoms are contemplated; in addition, the connector may be substituted by a halogen atom such as chlorine, bromine or fluorine. Thus, for example, C may be the diglycoyl residue, —CO—CH$_2$—O—CH$_2$—CO—, the succinoyl residue, —CO—CH$_2$—CH$_2$—CO—, thioglycoyl, —CO—CH$_2$—S—CH$_2$—CO or 1,4-terephthaloyl, —CO—C$_6$H$_4$—CO—.

The headgroup units, H$^1$ and H$^2$, are polar moieties (relative to the anchor) which, in combination with other parts of the amphiphile define the pore of the channel. In general, H$^1$ and H$^2$ may be the same or different and, in one embodiment, each has a fully extended length of about 3 to about 12 Angstroms. It is contemplated that multiple polar residues will be present. These residues, taken together, will be of sufficient polarity to comprise a headgroup for the amphiphilic system. Functional groups such as those found in amino acids and peptides are contemplated as are oxygen- and nitrogen-containing functionalities.

Headgroup units, $H^1$ and $H^2$ satisfying these design considerations, may be selected from a variety of organic units. For example, $H^1$ and $H^2$ may independently be substituted hydrocarbyl or heterocyclo. Typically, $H^1$ and $H^2$ will be substituted hydrocarbyl, bearing lower alkyl, ether, ester, thioester, amide, hydroxyl, thiol, amino, azo, halo, and other common organic polar substituents, each of which possesses a cumulative molecular weight not in excess of 150 a.m.u. In one embodiment, for example, $H^1$ and $H^2$ independently contain one or more peptide bonds.

As described in greater detail in the Examples presented below, in one embodiment $H^1$ and $H^2$ are peptides, each independently containing 1 to 7 amino acid residues. More typically, in this embodiment, $H^1$ and $H^2$ will contain 2 to 4 amino acid residues. Depending upon the type of ion channel to be formed by the amphiphile (anion or cation) and its degree of selectivity, the amino acid residues may be selected from any of the "standard" or "essential" α-amino acids, which serve as the building blocks for biological proteins, i.e., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine. Alternatively, in one embodiment, the amino acid residues may additionally be selected from "nonstandard" α-amino acids that can be found as components of certain proteins, e.g., 3-hydroxyproline, 4-hydroxyproline, ε-N,N,N-trimethyllysine, 3-methylhistidine, 5-hydroxylysine, O-phosphoserine, γ-carboxyglutamate, ε-N-acetyllysine, ω-N-methylarginine, N-acetylserine, N,N,N-trimethylalanine, N-formylmethionine, γ-aminobutyric acid, histamine, dopamine, thyroxine, citrulline, ornithine, β-cyanoalanine, homocysteine, azaserine, and S-adenosylmethionine. "Nonstandard" amino acids not specifically named are also contemplated. In one preferred embodiment, $H^1$ and $H^2$ are peptides containing the residues of α-amino acids having nonpolar side chains, e.g., alanine, glycine, isoleucine, leucine, methionine, proline, phenylalanine, tryptophan and valine. For example, in one embodiment $H^1$ and $H^2$ are tripeptides of α-amino acids having nonpolar side chains, e.g., GlyGlyGly.

To aid in the formation of a channel having a pore, the headgroups $H^1$ and $H^2$ are connected by a unit, B, which imparts a bend or kink to this region of the amphiphile. As a visualization aid (although not necessarily a completely accurate description of what is actually occurring), the unit, B, may be imagined to define a vertex formed at the intersection of headgroups $H^1$ and $H^2$ for a given amphiphile, with the assembly of two or more amphiphiles defining a polygon (i.e., the pore) having as its sides the headgroups $H^1$ and $H^2$ of the respective amphiphiles and having as its vertices the B units of the respective amphiphiles. In general, therefore, the unit, B, is preferably capable of directing (or holding) the two chains, $H^1$ and $H^2$ at an angle between about 30° and 150°; in one embodiment, it is preferred that the unit, B, be capable of directing (or holding) the two chains, $H^1$ and $H^2$ at an angle between about 60° and 120°. B units satisfying these design considerations may be selected from a variety of organic units. In general, these units are carbocyclic or heterocyclic. Non-cyclic B units are also contemplated although they may be poorer at holding the preferred conformation. For example, the B unit may be a 5 or 6-membered ring comprising carbon and optionally a nitrogen, oxygen, or sulfur ring atom wherein $H^1$ is covalently linked to one of the ring atoms and $H^2$ is covalently linked to another of the ring atoms. In this manner, $H^1$ and $H^2$ are directed (or held) at an angle. Exemplary B units include proline (attachment at carboxyl and amine moieties), pipecolic acid (attachment at carboxyl and amine moieties), Z-1,2-dicarboxycyclobutane (attachment at the two carboxyl groups), 2,5-dicarboxyfuran (attachment at the two carboxyl groups), 1,3-diaminobenzene (attachment at the amino groups).

The terminus, T, is generally any moiety that caps the amphiphile and is otherwise compatible with the chemistry used to assemble the amphiphile. Thus, T may be hydrocarbyl, substituted hydrocarbyl or heterocyclo. In those embodiments in which $H^2$ is a peptide, T is the C-terminal element. In combination with the carboxy function of the peptide, therefore, T may comprise an ether, ester, thioether, thioester, amide, thioamide or any of the various linkages containing oxygen, sulfur or nitrogen. For example, T may be a hydrocarbyl group such as alkyl, aryl, or aralkyl containing up to 20 carbon atoms, optionally substituted with an oxygen, nitrogen or sulfur containing moiety. Alternatively, T may be a heterocyclo moiety optionally substituted with an oxygen, nitrogen, or sulfur containing moiety. In one embodiment, $H^2$ is a peptide and T is a benzyloxy group ($-OCH_2C_6H_5$) at the C-terminus of the peptide (forming a terminal benzyl ester).

Although the mechanism is not yet precisely understood, the amphiphiles of the present invention have the ability to assemble in a lipid bilayer in such a manner that the assembly defines an ion channel. In general, the assembly will include two or more amphiphiles. And, as noted above, as a visualization aid (only) these amphiphiles may be thought to assemble in such a manner that the anchor unit holds the amphiphile in the lipid bilayer while the headgroup units of multiple amphiphiles assemble to define a polygon, with the B units of the respective amphiphiles defining vertices in the polygon, and the polygon serving as the pore of the channel. Thus, for example, the assembly of two amphiphiles may be thought to define a quadrilateral, the assembly of three amphiphiles may be thought to define a six-sided structure, etc.

Anion, particularly chloride ion, permeability is essential for volume, pH, and membrane potential regulation in all cells.[28,29] Currently, four major families of chloride channels are known.[30,31] Applicants have produced synthetic compounds that self-assemble, anchor and function as ion channels in cellular and cellular-like membranes. These assemblies are believed to comprise from 2 to about 20 amphiphiles (monomers). Moreover, applicants have succeeded in discerning from several lines of evidence a critical role for proline in the putative chloride entry portal. (1) All members of the CIC family of chloride protein channels contain the conserved motif GKXGPXXH (SEQ ID NO.: 8) in the anion pathway.[32] (2) Nicotinic acetylcholine receptors are converted to anion selectivity by the substitution of a proline into the intrinsic channel selectivity filter.[33,34] (3) Proline in channel forming peptides may form a "hinge-bend" regime,[35] GXXP, to extend the peptide across the membrane bilayer. (4) Proline may induce a surface "kink" in membrane transport proteins.[36] (5) The helix-loop-helix motif of C-peptide has proline at the loop's apex; this is required for ion channel activity.[37] (6) Peptides having a central proline form distinctive "toroidal pores" in bilayer membranes.[38]

In one embodiment, applicants have prepared a synthetic, chloride selective transporter, $[CH_3(CH_2)_{17}]_2$ NCOCH$_2$OCH$_2$CO-GGGPGGG-OCH$_2$Ph (SEQ ID NO.: 2), that is active in phospholipid bilayers.

In (C$_{18}$H$_{37}$)$_2$NCOCH$_2$OCH$_2$CO-GGGPGGG-OCH$_2$Ph (SEQ ID NO.: 2), the heptapeptide sequence places proline at the pinnacle of an "arch" flanked with glycine residues. Again, while not being bound to any theory for the working of this invention, applicants propose that the heptapeptide resides at the top of the midpolar regime to form an uncharged, chloride-selective portal, which is held in place by the hydrophobic anchor.[39]

Preparation of the Channel Mimics

Anchor-connector moieties such as (C$_{18}$H$_{37}$)$_2$NCOCH$_2$OCH$_2$COOH may be formed in a single step by heating equivalent amounts of diglycolic anhydride and bis(octadecyl)amine in refluxing toluene for 48 h. Evaporation of the solvent and crystallization from CHCl$_3$ afforded (C$_{18}$H$_{37}$)$_2$NCOCH$_2$OCH$_2$COOH as a colorless solid. The amphiphile, R$_2$NCOCH$_2$OCH$_2$CO-GGGPGGG-OCH$_2$Ph (SEQ ID NO.: 2) (first four lines), and an analog (last four lines) were prepared by a sequence of steps as shown.

R$_2$NCOCH$_2$OCH$_2$COOH+TsOH.H$_2$N-GGG-OCH$_2$Ph→R$_2$NCOCH$_2$OCH$_2$CO-GGG-OCH$_2$Ph→R$_2$NCOCH$_2$OCH$_2$CO-GGG-OH+ClH$_3$NPGGGOCH$_2$Ph→R$_2$NCOCH$_2$OCH$_2$CO-GGGPGGG-OCH$_2$Ph (SEQ ID NO.: 2)

R$_2$NCOCH$_2$OCH$_2$COOH +TsOH.H$_2$N-GGG-OCH$_2$Ph→R$_2$NCOCH$_2$OCH$_2$CO-GGG-OCH$_2$Ph→R$_2$NCOCH$_2$OCH$_2$CO-GGG-OH+ClH$_3$NLGGGOCH$_2$Ph→R$_2$NCOCH$_2$OCH$_2$CO-GGGLGGG-OCH$_2$Ph (SEQ ID NO.: 3)

The design, synthesis, and characterization of exemplary synthetic membrane transporters are described in detail in the Examples. These novel compounds impart ion permeability to phospholipid bilayers. For example, (C$_{18}$H$_{37}$)$_2$NCOCH$_2$OCH$_2$CO-GGGPGGG-OCH$_2$Ph (SEQ ID NO.: 2) inserts rapidly into liposomes and planar lipid bilayers. It forms a maximum 1.3±0.1 nS (nanoSiemens) chloride diffusion pathway (>10:1 Cl/K selectivity). (C$_{18}$H$_{37}$)$_2$NCOCH$_2$OCH$_2$CO-GGGPGGG-OCH$_2$Ph (SEQ ID NO.: 2) shows classic channel kinetic (open-close) behavior with clear evidence for voltage dependent gating. Data obtained to date (see Example 22 and FIG. 7), show that (C$_{18}$H$_{37}$)$_2$NCOCH$_2$OCH$_2$CO-GGGPGGG-OCH$_2$Ph (SEQ ID NO.: 2) also modulates cellular volume in mammalian cells. The diffusion based, ion channel behavior of this compound demonstrates that applicants' synthetic structures can afford selective membrane permeability equivalent in many respects to that seen in protein channels.

In another aspect of the invention, the concentration of a target anion is modulated by application of a channel mimetic as described above selective for the target anion to a cellular or other environment containing the target anion. In particular embodiments, anion concentration may be varied or regulated, e.g., to study the behavior of physiological systems or models thereof. Alternatively, they may be varied or regulated in therapeutic regimens, to increase or decrease anion concentrations in order to counteract or otherwise modify diseased or unwanted conditions. Accordingly, applicants' channel mimetics may be used to modulate the influx of anions, including, but not limited to halides such as chloride and bromide, or other anions such as nitrate, into a mammalian cell or other membrane compartments. Exemplary membrane compartments include mitochondria, endosomes, lysosomes, secretory vesicles, endoplasmic reticula, nucleii, Golgi apparatus, intracellular transport vesicles, MHC processing vesicles, reconstituted ruffled membrane vesicles from osteoclasts, and others having a phospholipid bilayer membrane.

In accordance with this aspect of the invention, a method of treating, preventing or ameliorating symptoms of a disease or condition associated with a cellular halide imbalance is provided. In this method, anion channel mimetics of the type described herein are inserted into the lipid bilayer of a mammalian cell in an appropriate amount, and manner, as determined by characteristics of the particular mimetic, patient profile, and disease in question.

In vivo, the invention may be applied to tissues such as the lungs, trachea, skin, muscle, brain, liver, heart, spleen, bone marrow, thymus, bladder, lymph, blood, pancreas, stomach, kidney, ovaries, testicles, rectum, peripheral or central nervous system, eyes, lymphoid organs, cartilage and endothelium. According to an advantageous choice of the invention, the target cell will be a muscle cell, a nerve cell, a hematopoietic stem cell or alternatively a cell of the airways, more particularly a tracheal or pulmonary cell, and advantageously a cell of the respiratory epithelium.

The following illustrates such a method. A channel mimetic is applied to the pulmonary epithelium by incorporation in an aerosolized particle of appropriate size. This application permits increased chloride permeability of the apical pulmonary epithelia. Increasing chloride permeability of apical membranes of pulmonary epithelia has been shown to reduce the pathophysiology associated with cystic fibrosis mutations.[40] Application of the chloride channel mimetic to the apical epithelium will be in sufficient concentration to increase chloride permeability and thereby compensate for cystic fibrosis mutations.

The amphiphiles of the present invention can be used as a medicament for curative or preventive purposes. More specifically, the amphiphiles may be used in a method of therapeutic treatment that consists of introducing the amphiphile into the phospholipid bilayer of target cells which are engaged in ion transport, in particular a mammalian cell, and more precisely a muscle cell, a hematopoietic stem cell, or a cell of the airways, more particularly a tracheal or pulmonary cell, or a cell of the respiratory epithelium. As such, the amphiphiles may be used in the preparation of a medicament for curative or preventive purposes, intended for the treatment of the human or animal body.

According to a first possibility, the medicament may be administered directly in vivo (for example into a muscle by infusion, into the lungs by aerosol and the like). It is also possible to adopt the ex vivo approach, which consists of collecting cells from the patient (bone marrow stem cells, peripheral blood lymphocytes, muscle cells, nerve cells epithelial cells and the like), administering the amphiphiles and re-administering the cells to the patient.

The amphiphiles of the present invention may be administered by the intramuscular, intratracheal, intranasal, intracerebral, intrapleural, intratumoral, intracardiac, intragastric, intraperitoneal, epidermal, intravenous or intraarterial route by a syringe or by any other equivalent means, systems suitable for the treatment of the airways or of the mucous membranes such as inhalation, instillation or aerosolization. There may also be mentioned the modes of administration by application of a cream, by oral administration or any other means known to the person skilled in the art and applicable to the present invention.

Administration may be achieved by a variety of different routes. One preferred route is oral administration of a composition such as a pill, capsule or suspension. Such compositions may be prepared according to any method known in the art, and may comprise any of a variety of inactive ingredients. Suitable excipients for use within such compositions include inert diluents (which may be solid materials, aqueous solutions and/or oils) such as calcium, potassium, or sodium carbonate, lactose, calcium, potassium, or sodium phosphate, water, arachis oil, peanut oil, liquid paraffin or olive oil; granulating and disintegrating agents such as maize starch, gelatin or acacia and/or lubricating agents such as magnesium stearate, stearic acid, or talc. Other inactive ingredients that may, but need not, be present include one or more suspending agents (e.g., sodium carboxymethylcellulose, methylcellulose, hydroxypropylmethylcellulose, sodium alginate, polyvinylpyrrolidone, gum tragacanth, and gum acacia), thickeners (e.g., beeswax, paraffin or cetyl alcohol), dispersing or wetting agents, preservatives (e.g., antioxidants such as ascorbic acid), coloring agents, sweetening agents and/or flavoring agents.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid, polyethylene glycols, polyethylene glycol ethers, and others known to those of ordinary skill in the art.

Particularly preferred are methods in which the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

Pharmaceutical compositions are administered in an amount, and with a frequency, that is effective to inhibit or alleviate the symptoms of a disease or condition such as cystic fibrosis and/or to delay the progression of the disease. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. It will be apparent that, for any particular subject, specific dosage regimens may be adjusted over time according to the individual need.

As noted above, a pharmaceutical composition may be administered to a mammal to stimulate chloride transport, and to treat cystic fibrosis. Patients that may benefit from administration of a therapeutic compound as described herein are those afflicted with cystic fibrosis. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport as provided herein.

In a further aspect, the invention provides methods of administering the pharmaceutical compositions of the present invention by intravenous, oral, instillation, inhalation, topical, intraperitoneal, subcutaneous, or intramuscular routes. The pharmaceutical compositions may be administered, for example, in the form of capsules, powders, tablets, liquids, solutions, and aerosolized solutions. Also within the practice of the invention are methods of treating diseases or other conditions in a mammal that give rise to defective anion transport across cell membranes.

Additional features and advantages of the invention will be set forth, and in part will be apparent from the description, or may be learned by practice of the invention. The objectives and other advantages of the invention will be realized and attained by the method particularly pointed out in the written description and claims herein as well as the appended drawings.

Additionally the compound of the present invention may be the active ingredient in a pharmaceutical composition that includes carriers, fillers, extenders, dispersants, creams, gels, solutions and other excipients that are common in the pharmaceutical formulatory arts.

Dosages of the compositions will vary, depending on factors such as half-life of the compound, potential adverse effects of the compound or of degradation products thereof, the route of administration, the condition of the patient, and the like. Such factors are capable of determination by those skilled in the art. The exact dose levels given on a daily basis, of course, is meant to be adapted by a physician to provide the optimum therapeutic response.

The following examples illustrate the invention:

EXAMPLES

Example 1

Synthesis of $(C_{18}H_{37})_2NCOCH_2OCH_2CO$-Gly-$OCH_2Ph$—Precursor

To a solution of $(C_{18}H_{37})_2NCOCH_2OCH_2COOH$ (1.0 g, 1.5 mmol) in $CH_2Cl_2$ (30 mL) was added 1-(3-dimethylaminopropyl)-3-ethyl carbodiimide hydrochloride (0.31 g, 1.6 mmol) and the reaction was stirred at room temperature. After 0.5 h, Gly-$OCH_2Ph$·TsOH (0.53 g, 1.5 mmol) and $Et_3N$ (0.6 mL) were added and the mixture was stirred overnight. The reaction mixture was washed with water (20 mL), 0.5 M aqueous HCl (20 mL), water (20 mL), 10% aqueous $Na_2CO_3$ (20 mL), and brine (20 mL) then dried over $MgSO_4$, evaporated and the residue crystallized from MeOH yielding $(C_{18}H_{37})_2NCOCH_2OCH_2CO$-Gly-$OCH_2Ph$ as a deliquescent white solid (0.86 g, 70%), mp 38–40° C. $^1$H-NMR (300 MHz, δ, $CDCl_3$) 0.86 (6H, t, J=6.9 Hz), 1.24 (64H, m), 1.50 (4H, bs), 3.06 (2H, t, J=7.5 Hz), 3.28 (2H, t, J=7.5 Hz), 4.10 (2H, s), 4.12 (2H, s), 4.25 (2H, s), 5.15 (2H, s), 7.33 (5H, m), 8.20 (1H, t, J=5.7 Hz). $^{13}$C-NMR (75 MHz, δ, $CDCl_3$): 14.2, 22.7, 26.9, 27.1, 27.6, 29.0, 29.39, 29.44, 29.5, 29.6, 29.7, 29.8, 32.0, 40.8, 46.3, 47.0, 67.1, 69.7, 71.8, 128.5, 128.6, 128.8, 135.3, 168.5, 169.8, 170.6.

Synthesis of $(C_{18}H_{37})_2NCOCH_2OCH_2CO$-Gly-Gly-$OCH_2Ph$—Precursor

To a solution of $(C_{18}H_{37})_2NCOCH_2OCH_2COOH$ (1.0 g, 1.5 mmol) in $CH_2Cl_2$ (30 mL) was added 1-(3-dimethylaminopropyl)-3-ethyl carbodiimide hydrochloride (0.31 g, 1.6 mmol) and the reaction was stirred at room temperature.

After 0.5 h Gly-Gly-OCH$_2$Ph.TsOH (0.62 g, 1.5 mmol) and Et$_3$N (0.6 mL) were added and the mixture was stirred overnight. The reaction mixture washed with water (20 mL), 0.5 M aqueous HCl (20 mL), water (20 mL), 10% aqueous Na$_2$CO$_3$ (20 mL), and brine (20 mL) then dried over MgSO$_4$, evaporated and the residue crystallized from MeOH to yield (C$_{18}$H$_{37}$)$_2$NCOCH$_2$OCH$_2$CO-Gly-Gly-OCH$_2$Ph as a deliquescent white solid (1.32 g, 94%). $^1$H-NMR (300 MHz, 6, CDCl$_3$) 0.87 (6H, t, J=6.9 Hz), 1.24 (64H, m), 1.48 (4H, bs), 3.05 (2H, t, J=7.5 Hz), 3.22 (2H, t, J=7.5 Hz), 4.06–4.10 (6H, m), 4.28 (2H, s), 5.15 (2H, s), 7.33 (5H, m), 7.51 (1H, t, J=5.7 Hz), 8.23 (1H, t, J=5.7 Hz). $^{13}$C-NMR (75 MHz, 6, CDCl$_3$): 14.2, 2.8, 27.0, 27.1, 27.6, 29.5, 29.7, 29.8, 32.0, 41.3, 42.8, 46.9, 67.1, 69.9, 72.2, 128.5, 128.7, 128.9, 135.6, 168.7, 169.9, 170.9.

Synthesis of TsOH.H$_2$N-Gly-Gly-Gly-OEt—Precursor

Glycyl-glycyl-glycine (2.0 g, 10.58 mmol), p-toluenesulfonic acid (2.2 g, 11.56 mmol) and ethanol (10 mL, 0.17 mol) were dissolved in toluene (50 mL) and the reaction was refluxed for 4 days in a flask connected to a Dean & Stark trap to remove water. The solvent was then evaporated then the residue was dissolved in methanol and ethyl ether was added until the product began to precipitate. The solution was kept in the refrigerator overnight and the copious precipitate formed was filtered and dried (3.4 g, 82.5%). mp 140–2° C. $^1$H-NMR (300 MHz, CDCl$_3$—CD$_3$OD≈9:1)): δ 1.05 (3H, t, J=7.2 Hz), 2.18 (3H, s), 3.65 (2H, s), 3.70 (2H, s), 3.77 (2H, s), 3.96 (2H, q, J=7.2 Hz), 6.99 (2H, d, J=8.1 Hz), 7.50 (2H, d, J=8.1 Hz). $^{13}$C-NMR (75 MHz, CDCl$_3$—CD$_3$OD≈9:1): δ 12.7, 20.9, 40.8, 40.9, 42.5, 42.6, 61.3, 125.5, 128.8, 140.7, 141.2, 167.1, 167.2, 170.1.

Synthesis of Boc-Pro-Gly-Gly-Gly-OEt. (SEQ ID NO.:1)—Precursor

A solution of Boc-L-Proline (0.35 g, 1.63 mmol) and H$_2$N-Gly-Gly-Gly-OEt tosylate (0.63 g, 1.62 mmol), 1-(3-dimethylaminopropyl)-3-ethyl carbodiimide hydrochloride (EDCI, 0.35 g, 1.83 mmol), 1-hydroxybenzotriazole (HOBt, 0.25 g, 1.85 mmol) and Et$_3$N (0.6 mL) in CH$_2$Cl$_2$ (50 mL) was cooled to 5° C. and stirred for 1 hour. The reaction was then stirred at ambient temperature for 2 days then the solvent was evaporated and the product was purified by column chromatography (SiO$_2$, CH$_2$Cl$_2$-MeOH 9:1→95:5) to give the final product (0.60 g, 87.6%) as a deliquescent solid. $^1$H-NMR (300 MHz, CDCl$_3$): δ 1.18 (3H, t, J=6.6 Hz), 1.35 (9H, s), 1.75–2.15 (4H, m), 3.40 (2H, m), 3.75–4.00 (7H, m), 4.09 (2H, q, J=7.2 Hz), 7.32 (2H, bs), 7.65 (2H, bs), 7.92 (2H, bs). $^{13}$C-NMR (75 MHz, CDCl$_3$): 614.2, 24.7, 28.4, 29.8, 41.3, 43.0, 43.3, 47.3, 60.7, 61.3, 77.4, 80.7, 155.6, 169.7, 169.8, 170.3, 174.1.

Synthesis of (C$_{18}$H$_{37}$)$_2$NCOCH$_2$OCH$_2$COOH—Precursor

A solution of dioctadecylamine (2.0 g, 3.8 mmol) and diglycolic anhydride (0.44 g, 3.8 mmol) was refluxed in toluene (50 mL) for 48 h. The solvent was then evaporated and the crude product recrystallized form CHCl$_3$ to give (C$_{18}$H$_{37}$)$_2$NCOCH$_2$OCH$_2$COOH as a white solid (2.12 g, 87%), mp 80–81° C. $^1$H-NMR (300 MHz, δ, CDCl$_3$): 0.87 (6H, t, J=6.9 Hz), 1.25 (64H, m), 1.55 (4H, bs), 3.07 (2H, t, J=7.8 Hz), 3.34 (2H, t, J=7.8 Hz), 4.21 (2H, s), 4.38 (2H, s). $^{13}$C-NMR (75 MHz, δ, CDCl$_3$): 14.2, 22.8, 26.9, 27.0, 27.5, 28.7, 29.4, 29.5, 29.6, 29.7, 29.8, 32.0, 47.0, 71.4, 73.2, 171.0, 172.2. IR (KBr, cm$^{-1}$): 1748 (CO), 1602 (CO).

Synthesis of (C$_{18}$H$_{37}$)$_2$NCOCH$_2$OCH$_2$CO-Gly-Gly-OCH$_2$Ph—Precursor To a solution of (C$_{18}$H$_{37}$)$_2$NCOCH$_2$OCH$_2$COOH (1.0 g, 1.5 mmol) in CH$_2$Cl$_2$ (30 mL) 1-(3-dimethylaminopropyl)-3-ethyl carbodiimide hydrochloride (0.31 g, 1.6 mmol) was added and the reaction was stirred at room temperature. After 0.5 h Gly-Gly-Gly-OCH$_2$Ph.TsOH (0.66 g, 1.5 mmol) and Et$_3$N (0.6 mL) were added and the mixture was stirred overnight. The reaction mixture was then washed with water (20 mL), 0.5 N HCl (20 mL), water (20 mL), 10% aqueous Na$_2$CO$_3$ (20 mL), brine (20 mL), and then dried over MgSO$_4$. The solvent was evaporated and the residue was crystallized form MeOH to yield (C$_{18}$H$_{37}$)$_2$NCOCH$_2$OCH$_2$CO-Gly-Gly-Gly-OCH$_2$Ph as a deliquescent white solid (1.26 g, 89%), mp 41–42° C. $^1$H-NMR (300 MHz, δ, CDCl$_3$) 0.86 (6H, t, J=6.9 Hz), 1.24 (64H, m), 1.49 (4H, bs), 3.04 (2H, t, J=7.5 Hz), 3.24 (2H, t, J=7.5 Hz), 3.95–4.05 (6H, m), 4.09 (2H, s), 4.29 (2H, s), 5.12 (2H, s), 7.23 (1H, t, J=6.0 Hz), 7.30–7.35 (5H, m), 7.93 (1H, t, J=5.7 Hz), 8.27 (1H, t, J=5.7 Hz). $^{13}$C-NMR (75 MHz, δ, CDCl$_3$): 13.9, 22.5, 26.7, 26.9, 27.4, 28.6, 29.2, 29.3, 29.6, 31.8, 41.0, 42.9, 46.3, 46.7, 66.9, 69.6, 71.7, 128.2, 128.4, 128.6, 135.3, 168.6, 169.7, 169.8, 170.0, 171.5. IR (KBr, cm$^{-1}$): 1749 (CO), 1651 (CO).

Synthesis of (C$_{18}$H$_{37}$)$_2$NCOCH$_2$OCH$_2$CO-Gly-Gly-Gly-OH—Precursor (C$_{18}$H$_{37}$)$_2$NCOCH$_2$OCH$_2$CO-Gly-Gly-Gly-OCH$_2$Ph (1.0 g, 1.1 mmol) was dissolved in absolute ethanol (100 mL), 10% Pd/C (0.2 g) was added, and this mixture was shaken under 70 psi hydrogen pressure for 3 h in a Parr apparatus. The reaction mixture was heated to reflux and filtered through a celite layer and the solvent was evaporated under reduced pressure to leave (C$_{18}$H$_{37}$)$_2$NCOCH$_2$OCH$_2$CO-Gly-Gly-Gly-OH as a white solid (0.86 g, 96%), mp 163–164° C. $^1$H-NMR (300 MHz, δ, CD$_3$OD): 0.90 (6H, t, J=6.9 Hz), 1.29 (64H, m), 1.57 (4H, bs), 3.21 (2H, t, J=7.8 Hz), 3.35 (2H, t, J=7.8 Hz), 3.93 (2H, s), 3.94 (2H, s), 3.97 (2H, s), 4.12 (2H, s), 4.40 (2H, s). IR (KBr, cm$^{-1}$): 1740 (CO), 1650 (CO).

Synthesis of Boc-Pro-Gly-Gly-Gly-OCH$_2$Ph. (SEQ ID NO.: 1)—Precursor

A solution of Boc-L-Proline (1.43 g, 6.7 mmol) and Gly-Gly-Gly-OCH$_2$Ph.TsOH (3.0 g, 6.7 mmol) in CH$_2$Cl$_2$ (40 mL) and Et3N (2.80 mL) was cooled to 5° C. and 1-(3-dimethylaminopropyl)-3-ethyl carbodiimide hydrochloride (1.34 g, 7.0 mmol) was added. The reaction was stirred at ambient temperature for 3 days and then the solvent was evaporated. The crude material was dissolved in ethyl acetate (50 mL) and washed with saturated aqueous NH$_4$Cl (25 mL), brine (25 mL), dried over MgSO$_4$, and then evaporated to dryness. The product was purified by column chromatography (SiO$_2$, CH$_2$Cl$_2$-MeOH 95:5) to give Boc-Pro-Gly-Gly-Gly-OCH$_2$Ph (SEQ ID NO.: 1) (2.25 g, 71%) as colorless crystals, mp 54–55° C. $^1$H-NMR (300 MHz, δ, CDCl$_3$): 1.42 (9H, s), 1.80–2.20 (4H, m), 3.35–3.55 (2H, m), 3.85–4.20 (7H, m), 5.15 (2H, s), 7.05 (2H, bs), 7.30–7.35 (5H, m), 7.80 (1H, bs). $^{13}$C-NMR (75 MHz, δ, CDCl$_3$): 24.6, 28.3, 29.4, 41.1, 43.0, 43.3, 47.2, 60.7, 66.9, 80.9, 128.4, 128.5, 128.7, 135.4, 155.8, 169.6, 170.0, 173.9. IR (KBr, cm$^{-1}$):, 1753(CO), 1667(CO).

Synthesis of Pro-Gly-Gly-Gly-OCH$_2$Ph. (SEQ ID NO.: 1)—Precursor

Boc-Pro-Gly-Gly-Gly-OCH$_2$Ph (SEQ ID NO.: 1) (0.2 g, 0.42 mmol) was dissolved in a 4N HCl solution in dioxane (10 mL) at 5° C. and the reaction mixture was stirred for 1 h at room temperature. The solvent was evaporated and the residue carefully dried at high vacuum and then crystallized from MeOH/Et$_2$O to give Pro-Gly-Gly-Gly-OCH$_2$Ph (SEQ ID NO.: 1) (0.18 g, 100%) as a colorless solid, mp 145–146°

C. $^1$H-NMR (300 MHz, δ, CD$_3$OD): 2.00–2.25 (4H, m), 3.35–3.45 (2H, m), 3.90–4.05 (6H, m), 4.30–4.40 (1H, m), 5.18 (2H, s), 7.30–7.40 (5H, m). $^{13}$C-NMR (75 MHz, δ, CD$_3$OD): 25.2, 30.9, 42.1, 43.3, 43.7, 47.6, 61.4, 68.1, 129.5, 129.6, 129.9, 137.5, 170.9, 171.4, 171.8, 172.4.

Example 2

Synthesis of (C$_{18}$H$_{37}$)$_2$NCOCH$_2$OCH$_2$CO-Gly-Gly-Gly-Pro-Gly-Gly-Gly-OCH$_2$Ph. (SEQ ID NO.: 2)

(C$_{18}$H$_{37}$)$_2$NCOCH$_2$OCH$_2$CO-Gly-Gly-GlyOH (0.31 g, 0.39 mmol) was suspended in CH$_2$Cl$_2$ (40 mL) and 1-(3-dimethylaminopropyl)-3-ethyl carbodiimide hydrochloride (0.08 g, 0.42 mmol) was added. The mixture was stirred for 0.5 h and Pro-Gly-Gly-Gly-OCH$_2$Ph.HCl (SEQ ID NO.: 1) (0.16 g, 0.39 mmol) in CH$_2$Cl$_2$ (10 mL) and Et$_3$N (0.15 mL) were added. The reaction mixture was stirred for 48 h at room temperature. The solvent was evaporated and the residue was recrystallized from MeOH to leave a white solid (0.37 g, 82%), mp 116–118° C. $^1$H-NMR (300 MHz, δ, CDCl$_3$): 0.87 (6H, t, J=6.9 Hz), 1.25 (64H, m), 1.47 (4H, bs), 1.80–2.20 (4H, m), 3.03 (2H, t, J=7.5 Hz), 3.23 (2H, t, J=7.5 Hz), 3.40–3.45 (1H, m), 3.50–3.55 (1H, m), 3.90–4.05 (12H, m), 4.12 (2H, s), 4.26 (2H, s), 4.35 (1H, bs), 5.12 (2H, s), 7.33 (5H, s), 7.66 (1H, bs), 7.76 (1H, bs), 7.85 (1H, bs), 8.06 (1H, bs), 8.31 (1H, bs), 8.47 (1H, bs). $^{13}$C-NMR (75 MHz, δ, CCl$_3$): 13.9, 22.5, 24.9, 26.8, 26.9, 27.5, 28.6, 29.2, 29.5, 29.6, 31.8, 41.1, 41.8, 42.5, 42.6, 42.8, 43.1, 46.1, 46.7, 61.1, 67.0, 69.1, 70.9, 128.2, 128.4, 128.6, 135.4, 168.5, 169.0, 170.3, 170.5, 170.6, 170.9, 171.2, 173.7. IR (KBr, cm$^{-1}$): 1740 (CO), 1653(CO).

Example 3

(H$_{21}$C$_{10}$)$_2$NCOCH$_2$OCH$_2$CO-Gly-Gly-Gly-Pro-Gly-Gly-Gly-OCH$_2$Ph. (SEQ ID NO.: 2)

This compound was prepared in analogy to the compound described in Example 2. The product was isolated as a white solid, mp 127–128° C.

Example 4

(H$_{29}$Cl$_4$)$_2$NCOCH$_2$OCH$_2$CO-Gly-Gly-Gly-Pro-Gly-Gly-Gly-OCH$_2$Ph. (SEQ ID NO.: 2)

This compound was prepared in analogy to the compound described in Example 2. The product was isolated as a white solid, mp 127–129° C.

Example 5

(H$_{33}$C$_{16}$)$_2$NCOCH$_2$OCH$_2$CO-Gly-Gly-Gly-Pro-Gly-Gly-Gly-OCH$_2$Ph. (SEQ ID NO.: 2)

This compound was prepared in analogy to the compound described in Example 2. The product was isolated as a white solid, mp 131–133° C.

Example 6

(H$_{37}$C$_{18}$)$_2$NCOCH$_2$OCH$_2$CO-Gly-Gly-Gly-Leu-Gly-Gly-Gly-OCH$_2$Ph. (SEQ ID NO.: 3)

This compound was prepared in analogy to the compound described in Example 2. The abbreviation "Leu" represents the amino acid leucine. The product was isolated as a white solid, mp 164–165° C.

Example 7

Synthetic Boc-Pip-Gly-Gly-Gly-OCH$_2$Ph Precursor (SEQ ID NO.: 4)

Boc-L-Pipecolic acid (Boc-Pip-OH, 0.50 g, 2.2 mmol), TsOH.H$_2$NGly-Gly-Gly-OCH$_2$Ph (0.98 g, 2.2 mmol), and Et$_3$N (1.50 mL) were dissolved in CH$_2$Cl$_2$ (20 mL) and cooled to 5° C. EDCl (0.46 g, 2.4 mmol) was added and reaction was stirred at ambient temperature for 3 days. Solvent was evaporated and residue was dissolved in EtOAc (50 mL) and washed with 5% citric acid (25 mL) Na$_2$CO$_3$ (25 mL) and brine (25 mL), dried over MgSO$_4$ and evaporated. The crude, oily product was purified by chromatography (SiO$_2$, 5% MeOH—CH$_2$Cl$_2$) and afforded colorless crystals (0.97 g, 91%). $^1$H-NMR CDCl$_3$: 1.45 (9H, s), 1.59 (4H, bs), 2.15 (2H, bs), 3.00 (1H, bs), 3.85–4.15 (7H, m), 4.69 (1H, s), 5.15 (2H, s), 6.96 (1H, bs), 7.10 (1H, bs), 7.30–7.50 (5H, m). $^{13}$C-NMR: 20.4, 24.7, 25.8, 28.3, 41.3, 42.6, 42.9, 43.2, 55.1, 67.2, 80.8, 128.3, 128.5, 128.6, 135.2, 156.1, 169.1, 169.6, 172.6. IR (KBr): 3325, 2938, 1752, 1664, 1530, 1457, 1409, 1366, 1253, 1189, 1164, 1032, 989, 870, 751, 699 cm$^{-1}$.

Example 8

Synthesis of (H$_{37}$C$_{18}$)$_2$N—CO—CH$_2$—O—CH$_2$—CO-Gly-Gly-Gly-Pip-Gly-Gly-Gly-OCH$_2$Ph (SEQ ID NO.: 5)

To 18$_2$DGA-Gly-Gly-Gly-OH (0.20 g, 0.25 mmol) suspended in CH$_2$Cl$_2$ (20 mL) 1-(3-dimethylaminopropyl)-3-ethyl carbodiimide hydrochloride (0.05 g, 0.28 mmol) and HOBt (0.04 g, 0.28 mmol) was added and reaction was stirred for 0.5 h. Then HCl.Pip-Gly-Gly-Gly-OCH$_2$Ph (0.12 g, 0.25 mmol) in CH$_2$Cl$_2$ (5 mL) containing NMM (0.05 mL, 0.46 mmol) was added and reaction mixture was stirred for 48 h at room temperature. Then solvent was evaporated and the residue was crystallized from MeOH to give (H$_{37}$C$_{18}$)$_2$N—CO—CH$_2$—O—CH$_2$—CO-Gly-Gly-Gly-Pip-Gly-Gly-Gly-OCH$_2$Ph (SEQ ID NO.: 5) as a white solid (0.24 g, 82%), mp 164–165° C. $^1$H-NMR CDCl$_3$: 0.87 (6H, t, J=6.9 Hz), 1.25 (64H, s), 1.50 (8H, bs), 2.13 (2H, bs), 2.85 (1H, bs) 3.05 (2H, t, J=7.5 Hz), 3.25 (2H, t, J=7.5 Hz), 3.55–3.65 (1H, m), 3.80–4.15 (12H, m), 4.10 (2H, s), 4.27 (2H, s), 5.04 (1H, bs), 5.14 (2H, s), 7.34 (5H, s), 7.49 (1H, bs), 7.55 (2H, bs), 7.85 (1H, bs), 7.98 (1H, bs), 8.29 (1H, bs). $^{13}$C-NMR: 14.1, 20.1, 22.7, 24.8, 25.8, 26.9, 27.1, 27.6, 29.3, 29.4, 29.6, 29.7, 31.9, 41.2, 41.4, 42.8, 43.0, 43.3, 46.3, 46.9, 50.7, 53.6, 67.0, 69.4, 71.3, 128.2, 128.4, 128.6, 135.4, 168.4, 169.4, 169.9, 170.0, 170.1, 170.3, 170.4, 170.9, 172.0. IR (KBr): 3315, 2921, 2851, 2359, 1749, 1656, 1541, 1468, 1262, 1130, 1029, 722, 698 cm$^{-1}$.

Example 9

(H$_{37}$C$_{18}$)$_2$N—CO—CH$_2$—O—CH$_2$—CO-Gly-Gly-Gly-Pro-Gly-Gly-Gly-OEt (SEQ ID NO.: 2) (H$_{37}$C$_{18}$)$_2$N—CO—CH$_2$—O—CH$_2$—CO-Gly-Gly-Gly-OH (0.43 g, 0.53 mmol) was suspended in CH$_2$Cl$_2$ (30 mL) and cooled to 0° C. 1-(3-dimethylaminopropyl)-3-ethyl carbodiimide hydrochloride (0.13 g, 0.68 mmol), 1-hydroxybenzotriazole (0.10 g, 0.74 mmol), Pro-Gly-Gly-Gly-OEt.HCl (SEQ ID NO.: 1) (0.19 g, 0.54 mmol) and Et$_3$N (0.6 mL) were added and the mixture was stirred for 0.5 h then the ice bath was removed and the reaction stirred for 48 h at room temperature. The solvent was then evaporated and the residue purified by column chromatography (silica, CHCl$_3$—CH$_3$OH 95:5→9:1) to give the final product as a white solid (0.22 g, 37.5%), mp 127–9° C. $^1$H-NMR (300 MHz, CDCl$_3$): δ 0.84 (9H, t, J=6.9 Hz), 1.22 (60H, m), 1.48 (4H, m), 1.85–2.21 (4H, m), 3.05 (2H, t, J=7.5 Hz), 3.23 (2H, t, J=7.2 Hz), 3.53 (1H, m), 3.60 (1H, m), 3.73–4.15 (16H, m), 4.26 (2H, s), 4.35 (1H, m), 7.53 (1H, bt), 7.59 (1H, bt), 7.91 (2H, m), 8.25 (2H, bt). $^{13}$C-NMR (75 MHz, CDCl$_3$): δ 14.2, 22.8, 25.3, 27.0, 27.2, 27.8, 29.0, 29.2, 29.5, 29.6, 29.7, 29.8, 32.0, 41.4, 42.0, 42.8, 43.0, 43.6, 46.4, 47.0, 61.3, 61.5, 69.5, 71.4, 168.5, 168.8, 170.3, 170.5, 170.9, 171.1, 173.7.

Example 10

(H$_{37}$C$_{18}$)$_2$NCOCH$_2$OCH$_2$CO-Gly-Gly-Gly-Pro-Gly-Gly-Gly-O(CH$_2$)$_6$CH$_3$. (SEQ ID NO.: 2)

This compound was prepared in analogy to the compound described in Example 10. The product was isolated as a white solid, mp 99–101° C.

Example 11

(H$_{37}$C$_{18}$)$_2$NCOCH$_2$OCH$_2$CO-Gly-Gly-Gly-Pro-Gly-Gly-Gly-OCH$_2$-c-C$_6$H$_{11}$. (SEQ ID NO.: 2)

This compound was prepared in analogy to the compound described in Example 10. The product was isolated as a white solid, mp 100–102° C.

Example 12

(H$_{37}$C$_{18}$)$_2$NCOCH$_2$OCH$_2$CO-Gly-Gly-Gly-Pro-Gly-Gly-Gly-OCH(CH$_3$)$_2$. (SEQ ID NO.: 2)

This compound was prepared in analogy to the compound described in Example 10. The product was isolated as a white solid, mp 129–131° C.

Example 13

(H$_{37}$C$_{18}$)$_2$NCOCH$_2$OCH$_2$CO-Gly-Gly-Gly-Pro-Gly-Gly-Gly-OCH$_2$CH$_3$. (SEQ ID NO.: 2)

This compound was prepared in analogy to the compound described in Example 10. The product was isolated as a white solid, mp 127–129° C.

Example 14

(H$_{37}$C$_{18}$)$_2$N—CO—CH$_2$—O—CH$_2$—CO-Gly-Gly-Gly-Pro-Gly-Gly-Gly-piperonylamine (SEQ ID NO.: 2)

To 18$_2$DGA-Gly-Gly-Gly-Pro-Gly-Gly-Gly-OH (SEQ ID NO.: 2) (0.14 g, 0.13 mmol) suspended in CH$_2$Cl$_2$ (5 mL) 1-(3-dimethylaminopropyl)-3-ethyl carbodiimide hydrochloride (0.03 g, 0.15 mmol), HOBt (0.02 g, 0.15 mmol) and NMM (0.03 mL, 0.25 mmol) was added and reaction was stirred for 0.5 h. Then piperonylamine (0.024 g, 0.15 mmol) was added and reaction mixture was stirred for 48 h at room temperature. Then solvent was evaporated and the residue was crystallized from MeOH to give the final product as colorless solid (0.12 g, 76%), $^1$H-NMR CDCl$_3$: 0.87 (6H, t, J=6.9 Hz), 1.25 (64H, s), 1.50 (4H, bs), 1.90–2.20 (4H, m), 3.06 (2H, t, J=7.5 Hz), 3.25 (2H, t, J=7.5 Hz), 3.40–3.45 (1H, m), 3.50–3.55 (1H, m), 3.80–4.40 (19H, m), 5.90 (2H, s), 6.70 (2H, s), 6.77 (1H, s), 7.61 (1H, bs), 7.66 (1H, br), 7.76 (1H, br), 7.84 (1H, bs), 7.90 (1H, bs), 8.05 (1H, bs), 8.26 (1H, bs). $^{13}$C-NMR: 14.0, 22.6, 25.0, 26.8, 27.0, 27.6, 28.8, 29.0, 29.3, 29.4, 29.5, 29.6, 31.8, 42.0, 42.7, 42.8, 42.9, 43.0, 43.3, 43.4, 43.5, 46.3, 46.9, 61.3, 69.3, 71.2, 100.9, 108.0, 108.3, 120.8, 132.5, 146.6, 147.6, 168.3, 168.8, 169.5, 170.1 170.2, 170.5, 170.8, 170.9, 173.4.

Example 15

Synthesis of an Amphiphile of the Form A-C—H$_1$-B-H$_2$-T Wherein R$_1$ and R$_2$ (of A) are not of Equal Length Synthesis 1—C$_{10}$H$_{21}$NHCOCH$_3$ To decylamine (6.5 g, 41.3 mmol) dissolved in dry CH$_2$Cl$_2$ (50 mL) acetic anhydride (3.8 g, 37.2 mmol) was added dropwise at 0° C. The reaction was stirred at room temperature overnight. The reaction mixture was washed with diluted aqueous HCl (2×50 mL), dried over MgSO$_4$ and solvent evaporated. The crude product was crystallized from hexanes to give white solid (7.30 g, 98%) mp 50–51° C. $^1$H-NMR CDCl$_3$: 0.87 (3H, t, J=6.6 Hz), 1.21 (14H, s), 1.44 (2H, m), 1.93 (3H, s), 3.16 (1H, t, J=7.0 Hz), 3.18 (1H, t, J=7.0 Hz), 5.98 (1H, bs). $^{13}$C-NMR: 14.0, 22.5, 23.1, 29.2, 29.4, 29.5, 31.8, 39.6, 170.1. IR (CHCl$_3$): 3284, 2925, 2916, 2871, 2850, 1641, 1566, 1466, 1380, 1298, 1171, 1110, 1001, 948, 957, 910, 852, 812, 786, 723 cm$^{-1}$.

Synthesis 2—C$_{10}$H$_{21}$NHCH$_2$CH$_3$

To LiAlH$_4$ (1.60 g, 42.2 mmol) suspended in dry THF (40 mL), C$_{10}$H$_{21}$NHCOCH$_3$ (5.6 g, 28.4 mmol) dissolved in THF (30 mL) was added dropwise and the reaction was refluxed for 48 h. The reaction was cooled down and ethyl acetate was added to decompose excess of LiAlH$_4$. The mixture was poured into diluted H$_2$SO$_4$ (250 mL) and extracted with Et$_2$O (2×100 mL). NaOH pellets were added to water phase to reach pH 10, and the mixture was extracted with Et$_2$O (3×50 mL). The organic phase was dried over MgSO$_4$ and solvent evaporated in vacuo. Bulb-to-bulb distillation using a Kugelrohr apparatus (85–89° C., 0.35 mm) gave 8.2 g (78%) of colorless oil. $^1$H-NMR CDCl$_3$: 0.87 (3H, t, J=6.6 Hz), 1.01 (1.5H, t, J=7.2 Hz), 1.11 (1.5H, t, J=7.2 Hz), 1.25 (14H, s), 1.48 (2H, m), 1.85 (1H, bs), 2.35–2.70 (4H, m). $^{13}$C-NMR: 11.6, 14.1, 15.2, 22.7, 26.9, 27.4, 27.7, 29.3, 29.5, 29.6, 30.1, 31.9, 44.1, 46.9, 49.9, 53.0. IR (neat): 3310, 3263, 3093, 2959, 2925, 2854, 2811, 1720, 1645, 1574, 1466, 1379, 1298, 1204, 1134, 1069, 722 cm$^{-1}$.

Synthesis 3—(H$_{21}$C$_{10}$)N(C$_2$H$_5$)—CO—CH$_2$—O—CH$_2$—CO—OH [(10,2)DGA-OH]

A solution of C$_{10}$H$_{21}$NHCH$_2$CH$_3$ (7.11 g, 38.4 mmol) and diglycolic anhydride (4.45 g, 38.4 mmol) in THF (60 mL) was refluxed for 24 h. The solvent was evaporated and the crude product was dissolved in Et$_2$O (150 mL) and washed with 10% aqueous HCl (2×20 mL). The acid was extracted with 10% NaOH (3×30 mL), and the water layer was acidified with concentrated aqueous HCl to pH 2, and it was extracted with CH$_2$Cl$_2$ (4×30 mL), dried (MgSO$_4$) and evaporated to give yellow oil (6.48 g, 56%) which was used in the next step without further purification. $^1$H-NMR CDCl$_3$: 0.87 (3H, t, J=6.6 Hz), 1.10–1.35 (17H, m), 1.55 (2H, m), 3.00–3.50 (4H, m), 4.21 (2H, s), 4.38 and 4.39 (2H, s). $^{13}$C-NMR: 12.6, 13.8, 14.1, 14.2, 22.6, 26.8, 26.9, 27.5, 28.7, 29.2, 29.3, 29.4, 29.5, 31.8, 41.3, 41.7, 46.4, 46.6, 71.0, 71.1, 72.8, 72.9, 170.4, 171.8. IR (neat): 2927, 2855, 1742, 1619, 1461, 1439, 1378, 1216, 1135, 1047, 972, 880, 794, 722 cm$^{-1}$.

Synthesis 4—(H$_{21}$C$_{10}$)N(C$_2$H$_5$)—CO—CH$_2$—O—CH$_2$—CO-Gly-Gly-Gly-OCH$_2$Ph To (10,2)DGA (1.43 g, 4.8 mmol) dissolved in CH$_2$Cl$_2$ (30 mL), 1-(3-dimethylaminopropyl)-3-ethylcarbodiimide hydrochloride (0.96 g, 5.0 mmol) and HOBt (0.70 g, 5.2 mmol) were added and the mixture was stirred at room temperature. After 0.5 h, TsOH.Gly-Gly-Gly-OCH$_2$Ph (2.15 g, 4.8 mmol) and Et$_3$N (3.0 mL) were added and reaction was stirred at ambient temperature overnight. The reaction mixture was evaporated in vacuo, the residue dissolved in ethyl acetate (50 mL) successively washed with 5% citric acid (20 mL), water (20 mL), 5% NaHCO$_3$ (20 mL), and brine (20 mL), dried (MgSO$_4$), evaporated. The crude, oily product was purified by chromatography (SiO$_2$, 10% MeOH—CH$_2$Cl$_2$) and afforded colorless oil (1.94 g, 73%). $^1$H-NMR CDCl$_3$: 0.86 (3H, t, J=6.6 Hz), 1.05–1.30 (17H, m), 1.50 (2H, bs), 3.00–3.35 (4H, m), 3.95–4.05 (6H, m), 4.09 (2H, s), 4.29 and 4.30 (2H, s), 5.13 (2H, s), 7.21 (1H, t, J=6.0 Hz), 7.30–7.40 (5H, m), 7.85–7.95 (1H, m), 8.27 (1H, t, J=6.0 Hz). $^{13}$C-NMR: 12.7, 13.9, 14.0, 22.6, 26.8, 27.0, 28.8, 29.2, 29.3, 29.4, 29.5, 29.6, 31.8, 41.2, 43.0, 45.9, 46.5, 67.0, 69.7, 71.7, 71.8, 128.2, 128.4, 128.6, 135.3, 168.3, 169.6, 169.7, 169.8, 169.9, 170.0, 171.3. IR (CHCl$_3$): 3302, 2926, 2855, 1749, 1656, 1541, 1457, 1358, 1260, 1193, 1129, 1032, 697 cm$^{-1}$.

Synthesis 5—(H$_{21}$C$_{10}$)N(C$_2$H$_5$)—CO—CH$_2$—O—CH$_2$—CO-Gly-Gly-Gly-OH (10,2)DGA-Gly-Gly-Gly-OCH$_2$Ph (2.3 g, 3.3 mmol) was dissolved in absolute ethanol (40 mL) and 10% Pd/C (0.13 g) was added and this mixture was shaken under 60 psi pressure of H$_2$ for 3 h. The reaction mixture was heated to reflux and filtered through a celite pad. The solvent was evaporated under reduced pressure to afford a white solid (1.50 g, 96%), mp 158–159° C. $^1$H-NMR CD$_3$OD: 0.90 (3H, t, J=6.6 Hz), 1.05–1.45 (17H, m), 1.56 (2H, bs), 3.15–3.40 (4H, m), 3.90–4.00 (6H, m), 4.11 (2H, s), 4.38 and 4.40 (2H, s). $^{13}$C-NMR: 13.2, 14.2, 14.6, 23.8, 28.0, 28.2, 28.8, 29.9, 30.6, 30.7, 30.8, 33.2, 41.9, 42.2, 42.5, 43.4, 43.5, 46.9, 47.0, 70.2, 70.3, 71.7, 170.6, 170.7, 172.2, 172.3, 172.9, 173.4. IR (CHCl$_3$): 2953, 2920, 2851, 1719, 1644, 1674, 1558, 1466, 1415, 1274, 1230, 1203, 1162, 1040, 1029, 908, 732, 651 cm$^{-1}$.

Synthesis 6—(H$_{21}$C$_{10}$)N(C$_2$H$_5$)—CO—CH$_2$—O—CH$_2$—CO-Gly-Gly-Gly-Pro-Gly-Gly-Gly-OCH$_2$Ph (SEQ ID NO.: 2)

To (10,2)DGA-Gly-Gly-Gly-OH (0.25 g, 0.52 mmol) suspended in CH$_2$Cl$_2$ (20 mL) 1,(3-dimethylaminopropyl)-3-ethyl carbodiimide hydrochloride (0.11 g, 0.57 mmol) and HOBt (0.08 g, 0.59 mmol) was added and reaction was stirred for 0.5 h. Then HCl.Pro-Gly-Gly-Gly-OCH$_2$Ph (SEQ ID NO.: 1) (0.22 g, 0.52 mmol) in CH$_2$Cl$_2$ (20 mL) containing Et$_3$N (0.15 mL) was added and reaction mixture was stirred for 48 h at room temperature. The reaction mixture was evaporated in vacuo, the residue successively washed with 5% citric acid (20 mL), water (20 mL), 5% NaHCO$_3$ (20 mL), and brine (20 mL), dried (MgSO$_4$), evaporated. The crude, oily product was purified by chromatography (SiO$_2$, 10% MeOH—CH$_2$Cl$_2$) and afforded a white solid (0.32 g, 75%) mp 195° C. (dec). [α]$_D^{23}$-17.7 (c 1.325, MeOH). $^1$H-NMR CDCl$_3$: 0.87 (3H, t, J=6.6 Hz), 1.05–1.35 (17H, m), 1.51 (2H, bs), 1.95–2.15 (4H, m), 3.00–3.40 (4H, m), 3.40–3.55 (2H, m), 3.70–4.40 (17H, m), 5.05–5.20 (2H, m), 7.30–7.40 (5H, m), 7.45–7.55 (2H, m), 7.85–8.00 (2H, m), 8.12 (1H, t, J=6.0 Hz), 8.30–8.40 (1H, bs). $^{13}$C-NMR: 13.0, 14.2, 14.3, 22.8, 25.3, 27.1, 27.3, 27.9, 29.2, 29.5, 29.6, 29.7, 32.1, 41.3, 41.5, 42.1, 42.3, 43.1, 43.2, 43.7, 46.0, 46.8, 47.1, 61.4, 67.3, 69.8, 71.6, 71.7, 128.5, 128.6, 128.8, 135.6, 168.5, 169.0, 170.3, 170.4, 170.5, 171.0, 171.1, 171.3, 173.6, 173.7. IR (CHCl$_3$): cm$^{-1}$. Anal. Calcd for C$_{40}$H$_{62}$N$_8$O$_{11}$: C, 57.82; H, 7.52; N, 13.48%. Found: C, 57.61; H, 7.56; N, 13.66%.

Example 16

(H$_{21}$C$_{10}$)N(C$_2$H$_5$)COCH$_2$OCH$_2$CO-Gly-Gly-Gly-Pro-Gly-Gly-Gly-OCH$_2$Ph. (SEQ ID NO.: 2)

This compound was prepared in analogy to the compound described in Example 16. The product was isolated as a white solid, mp 195° C. (dec).

Example 17

Synthesis of an Amphiphile of the Form A-C-H$_1$-B-H$_2$-T Wherein R$_1$ and R$_2$ (of A) are of Equal Length and B is a Methoxybenzoyl Unit.

Synthesis 1—N-Boc-3-amino-4-methoxybenzoic Acid.

3-Amino-4-methoxybenzoic acid (1.00 g, 6.0 mmol) was suspended in a 2:1 dioxane/water mixture (18 mL). After the addition of NEt$_3$ (0.8 mL) the mixture was cooled to 0° C. and di-tert-butyl-dicarbonate (1.57 g, 7.2 mmol) dissolved in dioxane (6 mL) was added dropwise over 30 minutes under stirring. The reaction was continued for 2 h at 5° C. and then overnight at room temperature. The dioxane was evaporated and the remaining solution was diluted with 5% Na$_2$CO$_3$ (35 mL) and washed twice with ethyl ether; the water phase was then acidified with 20% KHSO$_4$ and extracted with ethyl acetate then washed twice with water. The solvent was removed to give a solid (1.51 g, 94%), mp 197–198° C. $^1$H-NMR (300 MHz, DMSO-d6): δ 1.47 (9H, s), 3.88 (3H, s), 7.08 (1H, t, J=8.7 Hz), 7.66 (1H, dd, J=8.4 and 2.1 Hz), 8.06 (1H, s), 8.35 (1H, d, J=1.8 Hz), 12.62 (1H, bs). $^{13}$C-NMR (75 MHz, DMSO): δ 28.0, 56.0, 79.5, 110.5, 121.4, 122.8, 125.5, 127.3, 152.7, 152.8, 167.1.

Synthesis 2—N-Boc-3-Amino-4-methoxybenzoic Acid-Gly-Gly-Gly-OCH$_2$Ph (SEQ ID NO.: 6).

N-Boc-3-amino-4-methoxybenzoic acid (0.60 g, 2.22 mmol) was suspended in CH$_2$Cl$_2$ (40 mL) and added of 1-(3-dimethylaminopropyl)-3-ethyl carbodiimide hydrochloride (0.47 g, 2.44 mmol). The mixture was cooled to 0° C. and stirred for 0.5 h then Gly-Gly-Gly-OBz tosylate (1.00 g, 2.22 mmol) HOBt (0.33 g, 2.44 mmol) and Et$_3$N (0.9 mL) was added and the reaction stirred for 4 days at room temperature. The solvent was then evaporated and the residue purified by column chromatography (silica gel, CHCl$_3$/CH$_3$OH 97:3 to 95:5) to give a white solid (0.41 g, 35%), mp 66–67° C. $^1$H-NMR (300 MHz, CDCl$_3$): δ 1.50 (9H, s), 3.86 (3H, s), 3.94 (2H, d, J=6.0 Hz), 4.04 (4H, m), 5.10 (2H, s), 6.76 (1H, d, J=8.7 Hz), 7.02 (1H, s), 7.31 (5H, m), 7.45 (2H, m), 7.58 (2H, m), 8.42 (1H, bd). $^{13}$C-NMR (75 MHz, CCl$_3$): δ 28.3, 41.3, 43.0, 44.0, 55.8, 67.0, 80.8, 109.5, 116.3, 122.7, 125.8, 127.7, 128.2, 128.3, 128.6, 135.3, 150.1, 152.6, 168.0, 169.7, 169.9, 170.2.

Synthesis 3—18$_2$DGA-Gly-Gly-Gly-3-amino-4-methoxybenzoic Acid-Gly-Gly-Gly-OBz (SEQ ID NO.: 7).

N-Boc-3-amino-4-methoxybenzoic acid-Gly-Gly-Gly-OBz (SEQ ID NO.: 1) (0.40 g, 0.76 mmol) was dissolved in dioxane (15 mL), cooled to 0° C. and added of a 4N HCl solution in dioxane (4.0 mL). The homogeneous solution was stirred at room temperature under nitrogen atmosphere for 4 hours; the solvent was removed and the product carefully dried and used right away for the next reaction. This compound, HCl.3-amino-4-methoxybenzoic acid-Gly-Gly-Gly-OBz (SEQ ID NO.: 1) (0.16 g, 0.34 mmol) was added of 18$_2$DGA-Gly-Gly-Gly-OH (0.36 g, 0.44 mmol), PyCloP (0.19 g, 0.45 mmol) and dissolved in CH$_2$Cl$_2$. The mixture was cooled to 0° C. and added of diisopropylethylamine (0.16 mL, 0.92 mmol) and the resulting solution was stirred for 1 h. The reaction was then continued at room temperature for 4 days. The solvent was removed and the product purified by column chromatography (silica gel, CHCl$_3$/CH$_3$OH 95:5 to 8:2) to give a white solid (0.12 g, 28%), mp 124–6° C. $^1$H-NMR (300 MHz, CDCl$_3$/CD$_3$OD 9:1): δ 0.88 (6H, t, J=6.3 Hz), 1.26 (60H, m), 1.53 (4H, bs), 3.10 (2H, t, J=7.2 Hz), 3.30 (2H, t, J=7.2 Hz), 3.92 (3H, s), 4.04 (12H, m), 4.06 (2H, s), 4.12 (2H, s), 5.15 (2H, s), 6.88 (1H, d, J=9.0 Hz), 7.34 (5H, s), 7.63 (1H, dd, J=8.5 and 2.1 Hz), 8.48 (1H, d, J=1.8 Hz, ArH). $^{13}$C-NMR (75 MHz, CDCl$_3$): δ 14.3, 22.9, 27.1, 27.3, 27.8, 29.0, 29.5, 29.6, 29.8, 29.9, 32.1, 41.4, 43.1, 44.0, 44.0, 44.3, 44.3, 46.6, 47.1, 56.0, 67.1, 69.6, 71.7, 109.8, 118.4, 124.9, 125.9, 126.4, 128.3, 128.5, 128.7, 135.6, 150.9, 168.0, 168.3, 168.7, 170.1, 170.8, 171.2, 171.3.

Example 18

Synthesis 1—Dioctylcarbamoylmethoxyacetic Acid ((H$_{17}$C$_8$)$_2$N—CO—CH$_2$—O—CH$_2$—CO—OH; 8$_2$DGA).

A solution of dioctylamine (2.0 g, 8.3 mmol) and diglycolic anhydride (1.0 g, 9.13 mmol) was refluxed in toluene (30 mL) for 48 h. The solvent was then evaporated and the crude product dissolved in chloroform and washed with a diluted solution of HCl. The solvent was removed and the residue recrystallized form ethyl ether to give the final product as a white solid (2.1 g, 72.5%). Mp. 45–6° C. $^1$H-NMR (300 MHz, CDCl$_3$): δ 0.86 (6H, m), 1.26 (20H, m), 1.53 (4H, m), 3.07 (2H, t, J=7.8 Hz), 3.32 (2H, t, J=7.8 Hz), 4.19 (2H, s), 4.37 (2H, s). $^{13}$C-NMR (75 MHz, CDCl$_3$): 614.0, 22.5, 25.8, 26.7, 26.9, 27.3, 28.5, 29.0, 29.1, 29.2, 31.6, 31.7, 46.7, 46.8, 71.1, 72.8, 170.5, 171.8.

Synthesis 2—(H$_{17}$C$_8$)$_2$N—CO—CH$_2$—O—CH$_2$—CO-Gly-Gly-Gly-OCH$_2$Ph.

To a solution of 8$_2$DGA (0.5 g, 1.4 mmol) in CH$_2$Cl$_2$ (30 mL) cooled to 0° C., 1-(3-dimethylaminopropyl)-3-ethyl carbodiimide hydrochloride (0.3 g, 1.54 mmol), 1-hydroxybenzotriazole (0.21 g, 1.54 mmol), Gly-Gly-Gly-OBz tosylate (0.63 g, 1.4 mmol) and Et$_3$N (0.6 mL) were added and the reaction was stirred at room temperature for 2 days. The reaction was quenched and washed with a saturated solution of citric acid (20 mL), a saturated solution of NaHCO$_3$ (20 mL) and water (20 mL) then dried over MgSO$_4$, evaporated and the residue purified by column chromatography (silica, CHCl$_3$/CH$_3$OH 98:2) to give the pure final product as a deliquescent solid (0.76 g, 88%). $^1$H-NMR (300 MHz, CDCl$_3$) δ 0.86 (6H, m), 1.25 (20H, m), 1.50 (4H, m), 3.05 (2H, t, J=7.5 Hz), 3.25 (2H, t, J=7.5 Hz), 3.97–4.05 (6H, m), 4.10 (2H, s), 4.31 (2H, s), 5.14 (2H, s), 7.09 (1H, t, J=5.1 Hz), 7.34 (5H, m), 7.89 (1H, t, J=6.3 Hz), 8.27 (1H, t, J=6.0 Hz). $^{13}$C-NMR (75 MHz, CDCl$_3$): δ 14.0, 22.56, 22.59, 26.8, 27.0, 27.5, 28.8, 29.1, 29.2, 29.3, 31.7, 31.8, 41.1, 43.1, 46.4, 46.8, 67.0, 71.9, 128.2, 128.4, 128.6, 135.3, 168.5, 169.5, 169.6, 169.9, 171.4.

Synthesis 3—(H$_{17}$C$_8$)$_2$N—CO—CH$_2$—O—CH$_2$—CO-Gly-Gly-Gly-Pro-Gly-Gly-Gly-OCH$_2$Ph (8$_2$DGA-Gly-Gly-Gly-Pro-Gly-Gly-Gly-OBz) (SEQ ID NO.: 2)

8$_2$-DGA-Gly-Gly-Gly-OBz (1.0 g, 1.62 mmol) was dissolved in absolute ethanol (40 mL), 10% Pd/C (0.15 g) was added and this mixture was shaken under 70 psi hydrogen pressure for 3 h in a Parr apparatus. The reaction mixture was heated to reflux and filtrated through a celite layer then the solvent was evaporated under reduced pressure to leave a white solid in a quantitative yield (0.85 g, mp 125–7° C.).

This compound (0.3 g, 0.57 mmol) was suspended in CH$_2$Cl$_2$ (40 mL) then cooled to 0° C. and 1-(3-dimethylaminopropyl)-3-ethyl carbodiimide hydrochloride (0.12 g, 0.63 mmol), 1-hydroxybenzotriazole (0.08 g, 0.63 mmol), Gly-Gly-Gly-OBz tosylate (0.23 g, 0.57 mmol) and Et$_3$N (0.25 mL) were added and the reaction was stirred at room temperature for 2 days. The solvent was then evaporated and the residue recrystallized from MeOH to leave a white solid (0.25 g, 50%), mp 116–7° C. $^1$H-NMR (300 MHz, CDCl$_3$): δ 0.85 (6H, m), 1.24 (20H, m), 1.47 (4H, m), 1.85–2.20 (4H, m), 3.03 (2H, t, J=7.5 Hz), 3.24 (2H, t, J=7.5 Hz), 3.40–3.45 (1H, m), 3.75–4.07 (13H, m), 4.08 (2H, s), 4.25 (2H, s), 4.33 (1H, bs), 5.11 (2H, d, J=5.1 Hz), 7.32 (5H, s), 7.58 (2H, t), 7.93 (1H, t), 7.95 (1H, t), 8.26 (1H, m), 8.31 (1H, m). $^{13}$C-NMR (75 MHz, CCl$_3$): δ 14.2, 22.7, 25.3, 27.0, 27.2, 27.7, 29.0, 29.2, 29.3, 29.4, 29.5, 31.88, 31.94, 41.4, 42.0, 42.9, 43.0, 43.6, 46.4, 47.0, 61.3, 67.2, 69.2, 69.5, 71.4, 128.3, 128.5, 128.7, 135.6, 168.5, 168.9, 170.31, 170.38, 170.40, 170.6, 171.0, 171.1, 173.8.

Example 19

Synthesis 1—Didodecylcarbamoylmethoxyacetic Acid, ((H$_{25}$Cl$_2$)$_2$N—CO—CH$_2$—O—CH$_2$—CO—OH, 12$_2$DGA)

A solution of didodecylamine (1.0 g, 2.83 mmol) and diglycolic anhydride (0.3 g, 2.57 mmol) was refluxed in THF (50 mL) for 48 h. The solvent was then evaporated and the crude product dissolved in chloroform and washed with a diluted solution of HCl. The solvent was removed and the residue recrystallized form ethyl ether to give the final product as a white solid (1.20 g, 90.2%), mp 59–60° C. $^1$H-NMR (300 MHz, CDCl$_3$): δ 0.88 (6H, m), 1.26 (36H, m), 1.54 (4H, m), 3.07 (2H, t, J=7.8 Hz), 3.34 (2H, t, J=7.2 Hz), 4.20 (2H, s), 4.38 (2H, s). $^{13}$C-NMR (75 MHz, CDCl$_3$): δ 14.1, 22.6, 26.8, 26.9, 27.4, 28.6, 29.2, 29.3, 29.5, 31.9, 46.8, 71.2, 73.1, 170.3, 170.6.

Synthesis 2—(H$_{25}$C$_{12}$)$_2$N—CO—CH$_2$—O—CH$_2$—CO—OCH$_2$Ph, 12$_2$-DGA-Gly-Gly-Gly-OBz.

To a solution of 7 (0.17 g, 0.36 mmol) in CH$_2$Cl$_2$ (10 mL) cooled to 0° C., 1-(3-dimethylaminopropyl)-3-ethyl carbodiimide hydrochloride (0.076 g, 0.40 mmol), 1-hydroxybenzotriazole (0.054 g, 0.40 mmol), Gly-Gly-Gly-OBz tosylate (0.163 g, 0.36 mmol) and Et$_3$N (0.15 mL) were added and the reaction was stirred at room temperature for 2 days. The reaction was quenched and washed with a saturated solution of citric acid (20 mL), a saturated solution of NaHCO$_3$ (20 mL) and water (20 mL) then dried over MgSO$_4$, evaporated and the residue purified by column chromatography (silica, CHCl$_3$—CH$_3$OH 95:5) to give the pure final product as a deliquescent solid (0.15 g, 58%). $^1$H-NMR (300 MHz, CDCl$_3$) δ 0.88 (6H, m), 1.25 (36H, m), 1.51 (4H, m), 3.05 (2H, t, J=7.8 Hz), 3.26 (2H, t, J=7.5 Hz), 3.98–4.06 (6H, m), 4.10 (2H, s), 4.31 (2H, s), 5.14 (2H, s), 7.18 (1H, bs), 7.34 (5H, m), 7.94 (1H, t, J=5.7 Hz), 8.27 (1H, t, J=6.0 Hz). $^{13}$C-NMR (75 MHz, CDCl$_3$): δ 14.0, 22.5, 26.7, 26.9, 27.4, 28.6, 29.2, 29.3, 29.4, 29.5, 31.8, 41.0, 43.0, 46.3, 46.7, 66.9, 69.6, 71.8, 128.3, 128.4, 128.6, 135.3, 168.6, 169.7, 169.8, 170.1, 171.6.

Synthesis 3—(H$_{25}$C$_{12}$)$_2$N—CO—CH$_2$—O—CH$_2$—CO—OH, 12$_2$-DGA-Gly-Gly-Gly-OH.

12$_2$-DGA-Gly-Gly-Gly-OBz (0.15 g, 0.21 mmol) was dissolved in absolute ethanol (25 mL), 10% Pd/C (0.04 g) was added and this mixture was shaken under 70 psi hydrogen pressure for 3 h in a Parr apparatus. The reaction mixture was heated to reflux and filtrated through a celite layer then the solvent was evaporated under reduced pressure to leave a white solid in a quantitative yield (0.116 g), mp 122–3° C. $^1$H-NMR (300 MHz, $CD_3OD$): δ 0.95 (6H, t, J=6.6 Hz), 1.23 (36H, m), 1.45 (4H, m), 3.11 (2H, t, J=7.2 Hz), 3.19 (2H, t, J=7.2 Hz), 3.72–3.80 (6H, m), 3.97 (2H, s), 4.28 (2H, s), 8.17 (2H, m), 8.25 (1H, t, J=6.0 Hz). $^{13}$C-NMR (75 MHz, $CD_3OD$): 613.9, 22.1, 26.2, 26.4, 27.1, 28.3, 28.7, 29.0, 31.3, 41.6, 41.8, 45.1, 46.1, 68.8, 70.3, 168.3, 169.2, 169.4, 169.7, 171.4.

Synthesis 4—$(H_{25}C_{12})_2$N—CO—$CH_2$—O—$CH_2$—CO-Gly-Gly-Gly-Pro-Gly-Gly-Gly-$OCH_2$Ph, ($12_2$-DGA-Gly-Gly-Gly-Pro-Gly-Gly-Gly-OBz) (SEQ ID NO.: 2).

$12_2$-DGA-Gly-Gly-OH (0.10 g, 0.16 mmol) was suspended in $CH_2Cl_2$ (10 mL) and cooled to 0° C. then 1-(3-dimethylaminopropyl)-3-ethyl carbodiimide hydrochloride (0.033 g, 0.17 mmol), 1-hydroxybenzotriazole (0.023 g, 0.17 mmol), Gly-Gly-Gly-OBz tosylate (0.075 g, 0.16 mmol) and $Et_3N$ (0.10 mL) were added and the reaction was stirred at room temperature for 2 days. The solvent was then evaporated and the residue purified by column chromatography (silica, $CHCl_3/CH_3OH$ 95:5) and recrystallized from MeOH to leave a white solid (0.093 g, 59.6%), mp 111–2° C. $^1$H-NMR (300 MHz, $CDCl_3$): δ 0.87 (6H, t, J=6.3 Hz), 1.25 (36H, m), 1.48 (4H, m), 1.85–2.20 (4H, m), 3.08 (2H, t, J=7.5 Hz), 3.24 (2H, t, J=7.5 Hz), 3.48 (1H, m), 3.59 (1H, m), 3.77–4.17 (14H, m), 4.28 (2H, s), 4.34 (1H, bs), 5.14 (2H, d, J=3.9 Hz), 7.34 (5H, s), 7.46 (2H, m), 7.87 (3H, m), 8.37 (1H, bs). $^{13}$C-NMR (75 MHz, $CCl_3$): δ 14.2, 22.7, 25.3, 27.0, 27.2, 27.7, 29.0, 29.2, 29.3, 29.4, 29.5, 31.88, 31.94, 41.4, 42.0, 42.9, 43.0, 43.6, 46.4, 47.0, 61.3, 67.2, 69.2, 69.5, 71.4, 128.3, 128.5, 128.7, 135.6, 168.5, 168.9, 170.31, 170.38, 170.40, 170.6, 171.0, 171.1, 173.8.

Example 20

Experimental Results Illustrating That $(C_{18}H_{37})_2$NCOCH$_2$OCH$_2$CO-GGGPGGG-OCH$_2$Ph (SEQ ID NO.: 2) Mediates Cl$^-$ Release When Incorporated into Liposomes.

Liposomes were prepared by reverse-phase evaporation[26] as previously reported.[27] Cl$^-$ release was determined with a resin, chloride-specific electrode. Ion transport, mediated by $(C_{18}H_{37})_2$NCOCH$_2$OCH$_2$CO-GGGPGGG-OCH$_2$Ph (SEQ ID NO.: 2), was studied in unilamellar liposomes of 182±12 nm average dimension. Chloride release was rapid, concentration dependent, and went to completion in defined unilamellar liposomes (182±12 nm, FIG. 3). Replacement of the proline in $(C_{18}H_{37})_2$NCOCH$_2$OCH$_2$CO-GGG-OCH$_2$Ph by leucine (GGGPGGG (SEQ ID NO.: 2)→GGGLGGG) (SEQ ID NO.: 3)) dramatically reduced chloride efflux. The compound $(C_{18}H_{37})_2$NCOCH$_2$OCH$_2$CO-GGG-OCH$_2$Ph exhibited 6-fold reduced Cl$^-$ release. Neither the anchor-GGGLGGG (SEQ ID NO.: 3) compound nor the anchor-GGG compound retains the kink believed to be present in $(C_{18}H_{37})_2$NCOCH$_2$OCH$_2$CO-GGGPGGG-OCH$_2$Ph (SEQ ID NO.: 2) owing to the presence of the proline residue.

Substituting an impermeant external ion ($SO_4^=$) for a permeant one ($NO_3^-$) will generate a membrane potential that inhibits Cl$^-$ release. Thus, replacing nitrate by sulfate in the aqueous medium produced a 5-fold reduction in chloride efflux (data not shown). Addition of K$^+$-selective valinomycin reduced the membrane potential inhibition of net chloride movement and permitted the remaining chloride to exit the liposomes.

The chloride selectivity of $(C_{18}H_{37})_2$NCOCH$_2$OCH$_2$CO-GGGPGGG-OCH$_2$Ph (SEQ ID NO.: 2) was assessed by voltage clamp methods in planar phospholipid bilayers. Addition of $(C_{18}H_{37})_2$NCOCH$_2$OCH$_2$CO-GGGPGGG-OCH$_2$Ph (SEQ ID NO.: 2) to planar bilayer lipids produced large currents within seconds in a 450:150 mM KCl ion gradient. The sign and the magnitude of this current indicated Cl$^-$ transport by a nanoSiemen-sized channel. A linear current-voltage relationship gave a maximum conductance of 1.3±0.1 nS. The reversal potential, $E_{rev}$, was 28±0.45 mV, corresponding to the calculated chloride Nernst potential, $E_{Cl}$, of 28.2 mV. This confirms the >10:1 Cl$^-$/K$^+$ selectivity observed in liposomes. The ion selectivity and conductivity indicate that $(C_{18}H_{37})_2$NCOCH$_2$OCH$_2$CO-GGGPGGG-OCH$_2$Ph (SEQ ID NO.: 2) forms a large, stable, anion selective aqueous pore in bilayer membranes.

Example 21

Experimental Result Illustrating That $(C_{18}H_{37})_2$NCOCH$_2$OCH$_2$CO-GGGPGGG-OCH$_2$Ph (SEQ ID NO.: 2) Exhibits Voltage-dependent Gating When Incorporated Into Planar Lipid Bilayers.

Extensive biophysical studies have characterized the gating phenomenon in numerous proteins. Although a great deal is known about what occurs, the mechanism of gating is currently not understood. The behavior of $(C_{18}H_{37})_2$NCOCH$_2$OCH$_2$CO-GGGPGGG-OCH$_2$Ph (SEQ ID NO.: 2) is similar to that of numerous proteins in the sense that the behavior is modulated by the membrane potential.

Planar lipid bilayers were formed by standard methods. $(C_{18}H_{37})_2$NCOCH$_2$OCH$_2$CO-GGGPGGG-OCH$_2$Ph (SEQ ID NO.: 2) was applied to the cis chamber at 60 μM (micromolar) with a 450 mM/150 mM KCl gradient present across the membrane. Seconds later Cl$^-$ currents appeared and voltage was varied from +20 to −2 mV. Fractional open time was computed using the computer programs Fetchan and pStat (Axon Instruments, CA).

The compound $(C_{18}H_{37})_2$NCOCH$_2$OCH$_2$CO-GGG-PGGG-OCH$_2$Ph (SEQ ID NO.: 2) also exhibits voltage dependent gating, as illustrated in FIG. 4. The open time and current dependence upon membrane potential clearly demonstrate characteristic voltage gating by the $(C_{18}H_{37})_2$NCOCH$_2$OCH$_2$CO-GGGPGGG-OCH$_2$Ph (SEQ ID NO.: 2) anion current. The left panel shows characteristic channel transitions that progress from being continuously open to continuously closed, in a voltage dependent fashion. Using the data in the left panel, we calculated the dependence of channel open time as a function of membrane potential that is shown in the figure in the right panel. We note that in this case there is a strong dependence of open time on transmembrane voltage.

Example 22

The Effect of $(C_{18}H_{37})_2$NCOCH$_2$OCH$_2$CO-GGGPGGG-OCH$_2$Ph (SEQ ID NO.: 2) on Volume Regulation in a Monocytic Cell Line.

In eukaryotic cells regulatory volume decrease is mediated primarily by increasing separate conductive pathways for K$^+$ and Cl$^-$. Activating these pathways allows KCl and water to exit and reduce cellular volume. We therefore applied 45–100 μM concentrations of $(C_{18}H_{37})_2$NCOCH$_2$OCH$_2$CO-GGG-P-GGG-OCH$_2$Ph (SEQ ID NO.: 2) to cultured mammalian RAW 264.7 cells with the goal to test if increasing plasma membrane chloride permeability would generate a cellular volume decrease. We determined cell volume from 0.5 micron image stacks collected at 30 second intervals and calculated the time-dependent volume changes that are shown in FIG. 7B. There is a clear decrease in cell size that was consistently observed in these experiments when $(C_{18}H_{37})_2NCOCH_2OCH_2CO$-GGG-P-GGG-OCH$_2$Ph (SEQ ID NO.: 2) was applied to the cultured cells. The time course and extent of cell volume changes showed the decrease to be dose dependent, becoming 20–25% of the initial cell volume at concentrations of 100 µM $(C_{18}H_{37})_2$NCOCH$_2$OCH$_2$CO-GGG-P-GGG-OCH$_2$Ph (SEQ ID NO.: 2) (FIG. 7B). Selective inhibition of voltage dependent K$^+$-channels with quinine effectively blocks the cellular volume change (FIG. 7B) indicating no significant dependence upon neutral exchange mechanisms. Although small increases in cytosolic calcium were observed after the application of $(C_{18}H_{37})_2NCOCH_2OCH_2CO$-GGG-P-GGG-OCH$_2$Ph (SEQ ID NO.: 2) they were too late to indicate that secondary activation of endogenous Ca$^{2+}$ dependent potassium or chloride channels were responsible for the volume changes (FIG. 7C). We conclude that application of $(C_{18}H_{37})_2NCOCH_2OCH_2CO$-GGG-P-GGG-OCH$_2$Ph (SEQ ID NO.: 2) to cultured cells produces a rapid decrease in cellular volume, reflecting the increase in plasma membrane chloride permeability. We demonstrated that $(C_{18}H_{37})_2$NCOCH$_2$OCH$_2$CO-GGG-P-GGG-OCH$_2$Ph (SEQ ID NO.: 2) acts effectively as a chloride channel and predictably altered cellular physiology. The control of cellular volume is a complex process that involves the sensing of volume changes, signal transduction and alteration of membrane permeability. RAW 264.7 cells (American Type Culture Collection, Manassas Va.) were plated into microscope chambers in Dulbeccos Minimal Essential Media with antibiotics and 10% fetal calf serum and allowed to recover over night at 5% CO$_2$. Prior to experiment they were transferred to Hanks buffered saline (10 mM HEPES, pH 7.0) and placed into the thermostated microscope stage (37° C.) and permitted to equilibrate for 10 min. Cell volume was monitored and corrected for changes in cell geometry by optical sections at 0.5 micron steps from the glass surface to the top of the cell (typically 5–7 sections). Images were collected using a Zeiss 100 M Axovert microscope, a 12-bit Sensi-Cam, and analyzed using Slidebook 3.0 (Intelligent Imaging Innovations, Inc. Cambridge, Mass.). Cell volume was calculated by summing the intracellular surface for each image in the stack of sections. In FIG. 7A the images (40×) show cells before and 10 minutes after addition of 46 µM $(C_{18}H_{37})_2$ NCOCH$_2$OCH$_2$CO-GGG-P-GGG-OCH$_2$Ph (SEQ ID NO.: 2) (Note how the cell size changes in relation to the stationary markers "black dots"). In FIG. 7B the cellular volume changes were followed by comparing sequential series of z-stacks from optical sections and normalized to total cell volume at the beginning of the experiment (t=0). $(C_{18}H_{37})_2NCOCH_2OCH_2CO$-GGG-P-GGG-OCH$_2$Ph (SEQ ID NO.: 2) (46 µM) was added at t=0 and rapidly produced a 20% (S.D. ±0.5%) volume decrease (large open circle). Quinine (1 mM) which blocks potassium channels also required for volume change blocked the volume decrease (open square) in response to $(C_{18}H_{37})_2$ NCOCH$_2$OCH$_2$CO-GGG-P-GGG-OCH$_2$Ph (SEQ ID NO.: 2) addition. Untreated cells showed no significant change in volume. FIG. 7C shows that intracellular calcium changes are not temporally causing the observed volume changes. Intracellular calcium was followed using Fura-2 fluorescence ratio method. $(C_{18}H_{37})_2NCOCH_2OCH_2CO$-GGG-P-GGG-OCH$_2$Ph (SEQ ID NO.: 2) was applied at time zero to a concentration of 46 µM (small open circle) or 92 µM (inverted open triangle). Depolarization dependent increase in cytosolic calcium was initiated by the switch to 100 mM KCl at 200 seconds (open triangle). Changing membrane permeability selectively can affect a cellular volume increase or decrease because of the ion gradients that are established in eukaryotic cells. The volume change that we observed was 20±0.5% which is a significant change in volume and consistent with that observed by others for a potassium and chloride mediated volume decrease. The effective inhibition of the volume decrease mediated by $(C_{18}H_{37})_2NCOCH_2OCH_2CO$-GGG-P-GGG-OCH$_2$Ph (SEQ ID NO.: 2) following inhibition of voltage-dependent potassium channels with quinine also argues against activation of Ca$^{2+}$-dependent potassium channels and a major role for K$^+$-Na$^+$-2Cl$^-$ cotransport.

Example 23

Figure 8A:
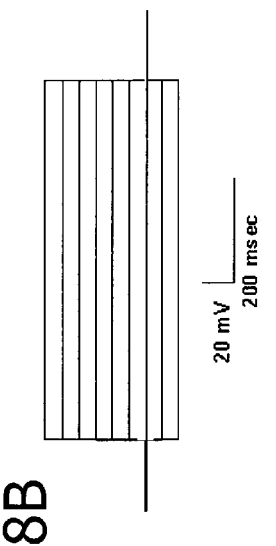
Figure 8B:
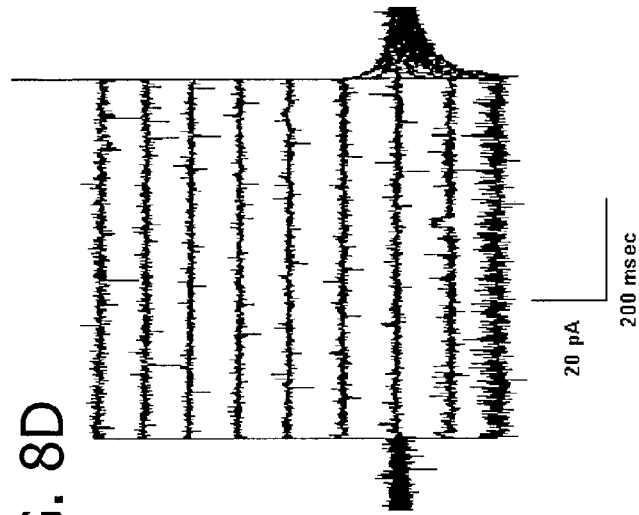
Figure 8C:
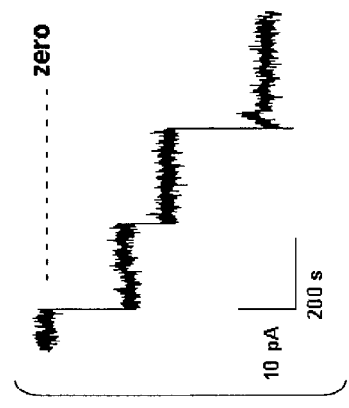
Figure 8D:
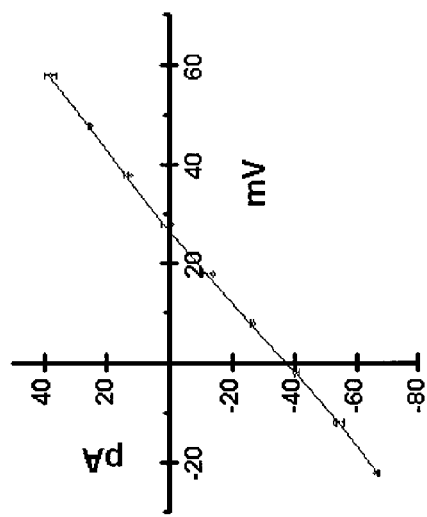

The chloride selectivity of $(C_{18}H_{37})_2NCOCH_2OCH_2CO$-GGG-P-GGG-OCH$_2$Ph (SEQ ID NO.: 2) was assessed by voltage clamp methods in planar lipid bilayers prepared as described in P. Schlesinger, et al., Proc. Natl. Acad. Sci. 94, 11357 (1997). The addition of 63 µM $(C_{18}H_{37})_2$ NCOCH$_2$OCH$_2$CO-GGG-P-GGG-OCH$_2$Ph (SEQ ID NO.: 2) produced large currents within seconds in a 450:150 mM KCl ion gradient (FIG. 8a). The sign of this current indicated Cl$^-$ transport by a nanoSiemen-sized channel and current-voltage plot and analysis revealed a conductance of 1.3±0.01 nS (FIG. 8b, 8d). The reversal potential, $E_{rev}$, was 28±0.45 mV, corresponding to the calculated chloride Nernst potential, $E_{Cl}$, of 28.2 mV (FIG. 8c). This confirms the >10:1 Cl$^-$/K$^+$ selectivity observed in liposomes. The ion selectivity and conductivity indicate that $(C_{18}H_{37})_2$ NCOCH$_2$OCH$_2$CO-GGG-P-GGG-OCH$_2$Ph (SEQ ID NO.: 2) forms a large, stable, anion selective aqueous pore in bilayer membranes.

Example 24

Fluorescence dequenching was used to study pore activation and size as previously described in Saito et al. CF dequenching reflects the kinetics of pore activation and dequenching is accurately fit by this equation.

$$F_t = F_0 + A_1(1-e^{-(t/\tau)}) + mt$$

Figure 9A:
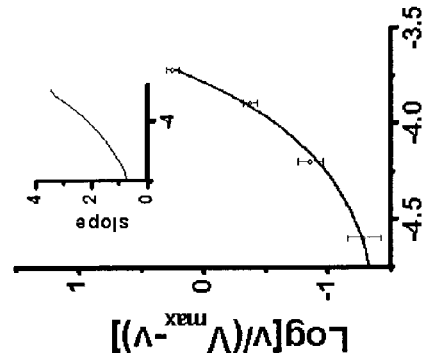
Figure 9B:
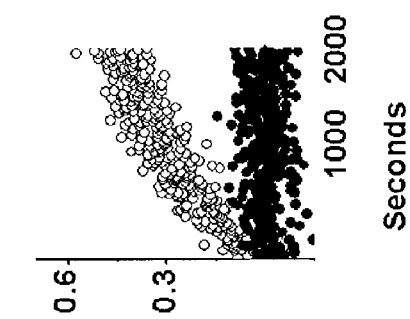
Figure 9C:
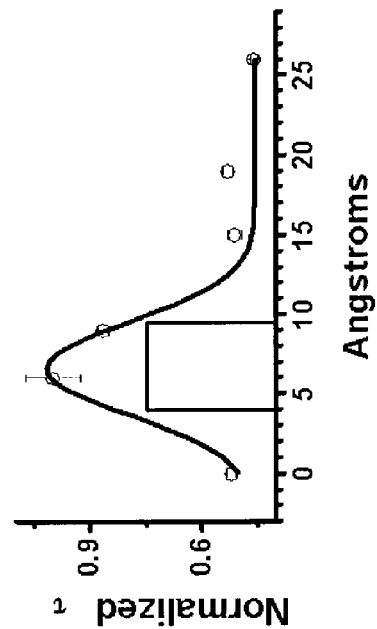
Figure 9D:
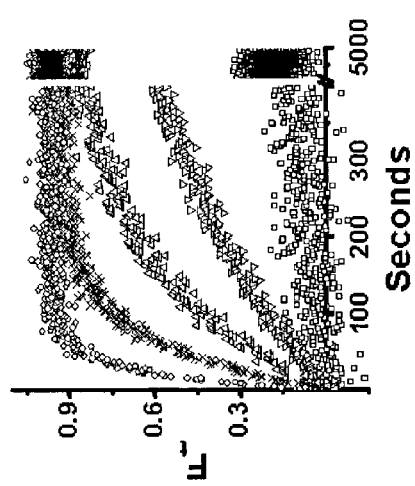
Figure 9E:
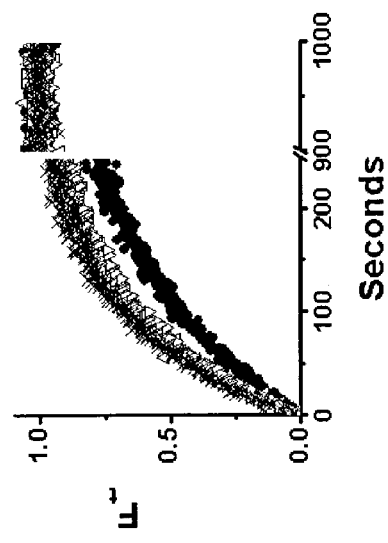

This exponential model requires that the concentration dependence of quenching will reflect the molecularity of pore activation (FIG. 9a, 9b). The concentration dependence of τ produced a Hill plot having a slope increasing from 0.8±0.5 to 3.6±0.6 (FIG. 9c) (I. Segel, *Enzyme Kinetics. Behavior and Analysis of Rapid Equilibrium and Steady-State Enzyme Systems* (John-Wiley & Sons, New York 1975), pp. 371–374). We infer therefore that at ~100 µM, the active pore involves two molecules of $(C_{18}H_{37})_2$ NCOCH$_2$OCH$_2$CO-GGG-P-GGG-OCH$_2$Ph (SEQ ID NO.: 2). Molecular models and bilayer conductance data suggested a pore diameter of 6.5–8 Å (D. Levitt, *Curr. Topics In Membranes and Transport* 21, 181 (1984); B. Hille, *J. Gen. Physiol.* 51, 199 (1968)). Size-specific dextran block (using ~6–26 Å diameter molecules) confirmed an apparent pore diameter of 6.6 A (FIG. 9d, 9e) (M. Saito, S. J. Korsmeyer, P. H. Schlesinger, *Nature Cell Biology*, 553 (2000); S. Rex, G. Schwarz, *Biochemistry* 37, 2336 (1998)). Taken together, molecular models, conductance data, and dextran block studies all suggest a pore size in the 6–8 Å range.

It is to be understood that the present invention has been described in detail by way of illustration and example in order to acquaint others skilled in the art with the invention, its principles, and its practical application. Further, the specific embodiments of the present invention as set forth are not intended to be exhaustive or to limit the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but put them forth only as possible explanations in light of current understanding.

Definitions and Abbreviations

To facilitate understanding of the invention, a number of terms are defined below. Any term not defined is understood to have the normal meaning used by scientists contemporaneous with the submission of this application. Certain abbreviations or other shorthand are described in the specification.

Abbreviations:

Å is Angstrom, also written Angstrom.

MBA is 3-amino-4-methoxybenzoic acid.

nS=nanoSiemen.

Pip is pipecolic acid.

pM=picoMole or picoMolar.

uM or µM=micromolar.

Anion: A negatively-charged ion.

Bilayer membrane: A bimolecular thick assembly that forms the permeability barrier surrounding eukaryotic cells and plays a similar role in intracellular compartments, liposomes, and other organelles. This membrane is comprised of any of a large number of amphipathic lipid molecules but in cells it is primarily comprised of phospholipids.

Cation: A positively-charged ion.

Cell: Cell according to the invention is understood to mean prokaryotic cells, yeast cells and eukaryotic cells, plant cells, human or animal cells, and in particular mammalian cells.

Channel: An aqueous diffusion pathway for membrane impermeant compounds usually formed by a pore within a membrane permitting the transfer of neutral or ionic species through it from one side of the membrane to the other.

Complex: A substance or species formed by association, aggregation, or organization of individual units that may be the same or different.

Liposome: An artificial sac, usually spherical, consisting of one (unilamellar) or more (multilamellar) bilayer membranes of phospholipid that encloses an aqueous core and in significant ways mimics biological membranes. The term liposome is sometimes used interchangeably with "vesicle."

Membrane: A thin, semi-permeable barrier that separates two liquid phases; said phases having the same or different compositions (see lipid bilayer above).

Midpolar regime: The portion of a phospholipid bilayer membrane that encompasses the glyceryl ester residues; distinguished from the hydrocarbon chains and the charged and/or polar headgroups Multilamellar: Used to indicate that the bilayer membrane of phospholipid liposomes consists of more than one concentric layer, structurally analogous to an onion.

Phospholipid membrane: A membrane (see above) barrier formed from phospholipid monomers.

Selectivity: Showing a measurable preference for one species over another, especially for cation over anion, anion over cation, one cation over a different cation, or one anion over a different anion.

Transport: The movement of an ion or other species across a membrane boundary.

Unilamellar: Used to indicate that the bilayer membrane of phospholipid liposomes consists of a single layer.

The term "amino" as used herein alone or as part of another group shall denote a primary, secondary or tertiary amine which may optionally be hydrocarbyl, substituted hydrocarbyl or heteroatom substituted. Specifically included are secondary or tertiary amine nitrogens which are members of a heterocyclic ring. Also specifically included, for example, are secondary or tertiary amino groups substituted by an acyl moiety.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" shall mean aryl or heteroaromatic.

The terms "aryl" or "ar" as used herein alone or as part of another group denote optionally substituted carbocyclic aromatic groups, preferably monocyclic or bicyclic groups containing from 6 to 12 carbon atoms in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroaromatic" as used herein alone or as part of another group denote optionally substituted aromatic groups having at least one carbon atom and at least a heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, thiazolyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrazolyl, pyrrolyl, indolyl, quinolinyl, thiazolyl, isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic, cyclic or aryl hydrocarbon groups, such as alkaryl, alkenaryl and alkynaryl. Unless otherwise indicated, these moieties preferably comprise 1 to 20 carbon atoms.

The "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. For example, substituents include moieties in which a carbon atom is substituted with a heteroatom such as nitrogen, oxygen, silicon, phosphorus, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

REFERENCES 1 (a) Aidley, D. J. & Stanfield, P. R. *Ion channels: Molecules in action*. Cambridge, Cambridge University Press, Cambridge, 1996. (b) Miller, C. *Current Opinion in Chemical Biology* 2000, 4, 148–151.

2. Hille, B. *Ionic channels of excitable membranes;* 3rd Edn.; Sinauer Associates: Sunderland, Mass., 2001.

3 Oiki, S., Danho, W., Montal, M. *Proc. Nat. Acad. Sci., (USA)* 1988, 85, 2393–2397.

4 Lear, J. D.; Wasserman, Z. R.; DeGrado, W. F. *Science* 1988, 240, 1177–1181.

5 Jullien, L.; Lehn, J.-M. *Tetrahedron Lett.* 1988, 3803–3806.

6 Mutter, M.; Altmann, K.-H.; Tuchscherer, G.; Vuilleumier, S. *Tetrahedron* 1988, 44, 771–785.

7 (a) Reusch, R. M. "Ion Recognition and Transport by Poly-(R)-3-hydroxybutanoates and Inorganic Polyphosphates," in G. W. Gokel (Ed.) *Advances in Supramolecular Chemistry*, volume 7, JAI Press, 2000, p. 49. (b) Das, S., Lengweiler, U. D., Seebach, D. & Reusch, R. N., *Proc. Nat. Acad. Sci. (USA)* 1997, 94, 9075–9079.

8 (a) Åkerfeldt, K.; Lear, J. D.; Wasserman, Z. R.; Chung, L. A.; DeGrado, W. F. *Acc. Chem. Res.* 1993, 26, 191–197. (b) Montal, M., *Annu. Rev. Biophys. Biomol. Struct* 1995, 24, 31–57.

9 Clark, T. D.; Buehler, L. K.; Ghadiri, M. R. *J. Am. Chem. Soc.* 1998, 120, 651–656.

10 (a) Voyer, N., & Robataille, M., *J. Amer. Chem. Soc.,* 1995. 117, 6599–6600. (b) Voyer, N., Potvin, L., & Rousseau, E., *J. C. S., Perkin Trans.* 2, 1997, 1469–1471.

11 Wagner, H., K. Harms, U. Koert, S. Meder and G. Boheim, *Angew. Chem. Int. Ed. Engl.* 1996, 35, 2643–2646.

12 Gokel, G. W. Chem. Comm. 2000, 1–9.

13 (a) Gokel, G. W., Murillo, O. *Acc. Chem. Res.* 1996, 29, 425–432. (b) Gokel, G. W.; Mukhopadhyay, A. *Chem. Soc. Rev.* 2001, 274–276. (c) Fyles, *Comprehensive Supramol. Chem.* 1996, vol. 10, 53–77.

14 Starostin, A. V., Butan, R., Borisenko, V., James, D. A., Wenschuh, H., Sansom, M. S. P., Woolley, G. A. *Biochemistry* 1999, 38, 6144–6150.

15 Boat, T. F. et al. in *The Metabolic Basis of Inherited Diseases,* Scriver, C. R. et al. (Eds.) McGraw-Hill, NY 1989.

16 Kerem, B. S., Rommens, J. M., Buchanan, J. A., Markiewicz, D., Cox, T. K., Chakravarti, A., Buchwald, M., Tsui, L. C. *Science* 1989, 245, 1073–1080.

17 Riordan J R, Rommens, J. M., Kerem, B., Alon, N., Rozmahel, R., Grzelczak, Z., Zielenski, J., Lok, S., Plavsic, N., Chou, J. L. *Science* 1989, 245, 1066–1073.

18 Rommens, J.; Iannuzzi, M.; Kerem, B.; Drumm, M.; Melmer, G.; Dean, M. R., R.; Cole, J.; Kennedy, D.; Hidaka, N.; Zsiga, M.; Buchwald, M.; Riordan, J.; Tusi, L.; Collins, F. *Science* 1989, 245, 1059–1065.

19 Hyde, S. C., Emsley, P., Hartshorn, M. J., Mimmack, M. M., Gileadi, U., Pearce, S. R., Gallagher, M. P., Gill, D. R., Hubbard, R. E., Higgins, C. F., *Nature* 1990, 346, 362–5.

20 Welsh M J *Science* 1986, 232, 1648–1650.

21 Frizzell, R. A., Rechkemmer, G., Shoemaker, R. L., *Science* 1986, 233, 558–560.

22 Welsh, M. J. and Liedtke, C. M. *Nature* 1986, 322, 467.

23 Li, M, McCann, J. D., Liedtke, C. M., Nairn, A. C., Greengard, P., Welsh, M. J.; *Nature* 1988, 331, 358–360.

24 Hwang, T. C., Lu, L., Zeitlin, P. L., Gruenert, D. C., Huganir, R., Guggino, W. B., *Science* 1989, 244, 1351–3.

25 (a) Schlesinger, P.H. "The use of intracellular parasites in the study of phagosomes and phagosome acidification." *Methods in Cell Biology,* 1994, Vol 45, D. Russell (Ed.). Academic Press, New York. 289–312. (b) Al-Awqati, Q. 1995 Chloride channels of intracellular Organelles. *Curr. Op. Cell Biol.* 504–508.

26 Szoka, F.; Papahadjopoulos, D. *Proc. Natl. Acad. Sci.* 1978, 75, 4194.

27 Saito, M.; Korsmeyer, S. J.; Schlesinger, P. H. *Nature Cell Biology,* 2000, 553.

28 Halm, D. R.; Frizzell, R. A. *Intestinal Chloride Secretion,* Raven, N.Y., 1990, pp. 47–58.

29 Steinmeyer, K.; Ortland, C; Jentsch, T. J. *Nature* 1991, 354, 301.

30 Fahlke, C; Yu, H.; Beck, C.; Rhodes, T.; George, A. *Nature* 1997, 390, 529.

31 Fahlke, C.; Desai, R. R.; Gillani, N.; George, A. L. *J. Biol. Chem.* 2001, 276, 1759.

32 Corringer, P. J.; Bertrand, S.; Galzi, J.; Devillers-Thiery, A.; Changeux, J.-P.; Bertrandt, D. *Neuron* 1999, 22, 831–843.

33 Galzi, J. L.; Devillers-Thiery, A.; Hussy, N.; Bertrand, S.; Changeux, J. P.; Bertrand, D. *Nature* 1992, 359, 500–505.

34 Gibbs, N.; Sessions, R. B.; Williams, P. B.; Dempsey, C. E. *Biophys. J.* 1997, 72, 2490.

35 Brandl, C. J.; Deber, C. M. *Proc. Natl. Acad. Sci. USA* 1986, 83, 917.

36 Ido, Y.; Vindigni, A.; Chang, K.; Stramm, L.; Chance, R.; Heath, W. F.; DiMarchi, R. D.; DiCera, E.; Williamson, J. R. *Science* 1997, 277, 563–566.

37 Yang, L.; Harroun, T. A.; Weiss, T. M.; Ding, L.; Huang, H. W. *Biophys. J.* 2001, 81, 1475–1485.
38 Berendsen, H. J. C. *Biophys. J.* 1999, 76, 40.
39 Merlin, D.; Yue, G.; Lencer, W. I.; Selsted, M. E.; Madara, J. L. *Am. J. Physiol. Cell Physiol.* 2001, 280, C296–C302.

All publications, patents, patent applications or other references cited in this application are herein incorporated by reference in their entirety as if each individual publication, patent, patent application or reference is specifically and individually indicated to be incorporated by reference.

What is claimed is:

1. An amphiphile for the formation of a synthetic ion channel in a phospholipid bilayer membrane, the amphiphile corresponding to the formula $A-C-H^1-B-H^2-T$ wherein A is hydrocarbyl or —$NR^1R^2$ linked to the connector, C, optionally through a nitrogen, oxygen or sulfur atom;

each of $R^1$ and $R^2$ are independently hydrocarbyl or substituted hydrocarbyl;

C is a single covalent bond or a hydrocarbyl, substituted hydrocarbyl or heterocyclo;

$H^1$ is substituted hydrocarbyl, heterocyclo, or peptide, provided that $H^1$ contains at least one glycine residue;

B is substituted hydrocarbyl, carbocyclic, or heterocyclo;

$H^2$ is substituted hydrocarbyl, heterocyclo, or peptide, provided that $H^2$ contains at least one glycine residue; and T is hydrocarbyl, substituted hydrocarbyl or heterocyclo.

2. The amphiphile of claim 1 wherein A is hydrocarbyl.

3. The amphiphile of claim 1 wherein A is —$NR^1R^2$ and each of $R^1$ and $R^2$ are independently hydrocarbyl or substituted hydrocarbyl.

4. The amphiphile of claim 1 wherein A is —$NR^1R^2$, each of $R^1$ and $R^2$ are independently hydrocarbyl or substituted hydrocarbyl, and C is substituted hydrocarbyl comprising ether, thioether, carbonyl, or thiocarbonyl.

5. The amphiphile of claim 1 wherein A is —$NR^1R^2$, each of $R^1$ and $R^2$ are independently hydrocarbyl or substituted hydrocarbyl, and $H^1$ or $H^2$ comprises three consecutive glycine residues.

6. The amphiphile of claim 1 wherein A is —$NR^1R^2$, each of $R^1$ and $R^2$ are independently hydrocarbyl or substituted hydrocarbyl, and each of $H^1$ and $H^2$ comprise three consecutive glycine residues.

7. The amphiphile of claim 1 wherein A is —$NR^1R^2$, each of $R^1$ and $R^2$ are independently hydrocarbyl or substituted hydrocarbyl, C is substituted hydrocarbyl comprising ether, thioether, carbonyl, or thiocarbonyl and each of $H^1$ and $H^2$ are peptides containing the residues of α-amino acids selected from the group consisting of alanine, glycine, isoleucine, leucine, methionine, phenylalanine, tryptophan and valine.

8. The amphiphile of claim 1 wherein A is —$NR^1R^2$, each of $R^1$ and $R^2$ are independently hydrocarbyl or substituted hydrocarbyl, and each of $H^1$ and $H^2$ are peptides containing 1 to 7 residues of α-amino acids selected from the group consisting of alanine, glycine, isoleucine, leucine, methionine, phenylalanine, tryptophan and valine.

9. The amphiphile of claim 1 wherein A is —$NR^1R^2$, each of $R^1$ and $R^2$ are independently hydrocarbyl or substituted hydrocarbyl, and B is an optionally substituted 5- or 6-membered ring comprising carbon and optionally at least one nitrogen, oxygen, or sulfur ring atom wherein $H^1$ is covalently linked to one of the ring atoms and $H^2$ is covalently linked to another of the ring atoms.

10. The amphiphile of claim 1 wherein A is —NR$^1$R$^2$, each of R$^1$ and R$^2$ are independently hydrocarbyl or substituted hydrocarbyl, each of H$^1$ and H$^2$ are peptides comprising the residue of α-amino acid residues selected from the group consisting of alanine, glycine, isoleucine, leucine, methionine, phenylalanine, tryptophan and valine, and B is an optionally substituted 5- or 6-membered ring comprising carbon and optionally at least one nitrogen, oxygen, or sulfur ring atom wherein H$^1$ is covalently linked to one of the ring atoms and H$^2$ is covalently linked to another of the ring atoms.

11. The amphiphile of claim 1 wherein A is —NR$^1$R$^2$, each of R$^1$ and R$^2$ are independently hydrocarbyl or substituted hydrocarbyl, C is substituted hydrocarbyl comprising ether, thioether, carbonyl, or thiocarbonyl, each of H$^1$ and H$^2$ comprise the residue of at least one α-amino acid independently selected from the group consisting of alanine, glycine, isoleucine, leucine, methionine, phenylalanine, tryptophan and valine, and B is a 5- or 6-membered ring with H$^1$ being covalently bonded to one of the ring atoms and H$^2$ being covalently bonded to another of the ring atoms, the 5 or 6-membered ring being selected from the group consisting of optionally substituted residues of proline, pipecolic acid, Z-1,2-dicarboxycyclobutane, 2,5-dicarboxyfuran, and 1,3-diaminobenzene.

12. The amphiphile of claim 1 wherein A is —NR$^1$R$^2$, each of R$^1$ and R$^2$ are independently hydrocarbyl or substituted hydrocarbyl, C is substituted hydrocarbyl comprising ether, thioether, carbonyl, or thiocarbonyl, each of H$^1$ and H$^2$ comprise the residue of at least one α-amino acid independently selected from the group consisting of alanine, glycine, isoleucine, leucine, methionine, phenylalanine, tryptophan and valine, and B is the residue of proline or 4-hydroxyproline.

13. The amphiphile of claim 1 wherein
A is dialkylamino in which the alkyl groups are normal alkyl groups, they are the same or different, and range from CH$_3$ to C$_{18}$H$_{37}$;
C is —COCH$_2$OCH$_2$CO—;
B is selected from the group consisting of leucine, proline, pipecolic acid, and 3-amino-4-methoxybenzoic acid; and
T is selected from the group consisting of ethyl ester, isopropyl ester, n-heptyl ester, cyclohexylmethyl ester, and benzyl ester.

14. An amphiphile for the formation of a synthetic ion channel in a phospholipid bilayer membrane, the amphiphile corresponding to the formula

A-C-H$^1$-B-H$^2$-T wherein
A is hydrocarbyl, substituted hydrocarbyl, heterocyclo or amino linked to the connector, C, optionally through a nitrogen, oxygen or sulfur atom;
C is substituted hydrocarbyl comprising ether, thioether, carbonyl, or thiocarbonyl;
H$^1$ is substituted hydrocarbyl, heterocyclo, or peptide, provided that H$^1$ contains at least one glycine residue;
B is substituted hydrocarbyl, carbocyclic, or heterocyclo;
H$^2$ is substituted hydrocarbyl, heterocyclo, or peptide, provided that H$^2$ contains at least one glycine residue; and
T is hydrocarbyl, substituted hydrocarbyl or heterocyclo.

15. The amphiphile of claim 14 wherein C comprises a diglycoyl, succinoyl, thioglycoyl, or 1,4-terephthaloyl.

16. The amphiphile of claim 14 wherein A is —NR$^1$R$^2$, each of R$^1$ and R$^2$ are independently hydrocarbyl or substituted hydrocarbyl, and H$^1$ or H$^2$ comprises three consecutive glycine residues.

17. The amphiphile of claim 14 wherein A is —NR$^1$R$^2$, each of R$^1$ and R$^2$ are independently hydrocarbyl or substituted hydrocarbyl, and each of H$^1$ and H$^2$ comprise three consecutive glycine residues.

18. The amphiphile of claim 14 wherein A is —NR$^1$R$^2$, each of R$^1$ and R$^2$ are independently hydrocarbyl or substituted hydrocarbyl, and each of H$^1$ and H$^2$ are peptides containing 1 to 7 residues of α-amino acids selected from the group consisting of alanine, glycine, isoleucine, leucine, methionine, phenylalanine, tryptophan and valine.

19. An amphiphile for the formation of a synthetic ion channel in a phospholipid bilayer membrane, the amphiphile corresponding to the formula

A-C-H$^1$-B-H$^2$-T wherein
A is hydrocarbyl;
C is a single covalent bond or a hydrocarbyl, substituted hydrocarbyl or heterocyclo;
H$^1$ is substituted hydrocarbyl, heterocyclo, or peptide, provided that H$^1$ contains at least one glycine residue;
H$^2$ is substituted hydrocarbyl, heterocyclo, or peptide, provided that H$^2$ contains at least one glycine residue;
B is an optionally substituted 5- or 6-membered ring comprising carbon and optionally at least one nitrogen, oxygen, or sulfur ring atom wherein H$^1$ is covalently linked to one of the ring atoms and H$^2$ is covalently linked to another of the ring atoms; and
T is hydrocarbyl, substituted hydrocarbyl or heterocyclo.

20. The amphiphile of claim 19 wherein B is a 5 or 6-membered ring with H$^1$ being covalently bonded to one of the ring atoms and H$^2$ being covalently bonded to another of the ring atoms, the 5- or 6-membered ring being selected from the group consisting of optionally substituted residues of proline, pipecolic acid, Z-1,2-dicarboxycyclobutane, 2,5-dicarboxyfuran, and 1,3-diaminobenzene.

21. The amphiphile of claim 19 wherein A is —NR$^1$R$^2$, each of R$^1$ and R$^2$ are independently hydrocarbyl or substituted hydrocarbyl, and H$^1$ or H$^2$ comprises three consecutive glycine residues.

22. The amphiphile of claim 19 wherein A is —NR$^1$R$^2$, each of R$^1$ and R$^2$ are independently hydrocarbyl or substituted hydrocarbyl, and each of H$^1$ and H$^2$ comprise three consecutive glycine residues.

23. The amphiphile of claim 19 wherein A is —NR$^1$R$^2$, each of R$^1$ and R$^2$ are independently hydrocarbyl or substituted hydrocarbyl, and each of H$^1$ and H$^2$ are peptides containing 1 to 7 residues of α-amino acids selected from the group consisting of alanine, glycine, isoleucine, leucine, methionine, phenylalanine, tryptophan and valine.

24. An amphiphile for the formation of a synthetic ion channel in a phospholipid bilayer membrane, the amphiphile corresponding to the formula

A-C-H$^1$-B-H$^2$-T wherein
A is hydrocarbyl, substituted hydrocarbyl, heterocyclo or amino linked to the connector, C, optionally through a nitrogen, oxygen or sulfur atom;
C is substituted hydrocarbyl comprising ether, thioether, carbonyl, or thiocarbonyl;
H$^1$ is substituted hydrocarbyl, heterocyclo, or peptide, provided that H$^1$ contains at least one glycine residue;

B is substituted hydrocarbyl, carbocyclic, or heterocyclo;
H$^2$ is substituted hydrocarbyl, heterocyclo, or peptide, provided that H$^2$ contains at least one glycine residue; and
T is benzyl or benzyloxy.

25. The amphiphile of claim 24 wherein A is —NR$^1$R$^2$, each of R$^1$ and R$^2$ are independently hydrocarbyl or substituted hydrocarbyl, and H$^1$ or H$^2$ comprises three consecutive glycine residues.

26. The amphiphile of claim 24 wherein A is —NR$^1$R$^2$, each of R$^1$ and R$^2$ are independently hydrocarbyl or substituted hydrocarbyl, and each of H$^1$ and H$^2$ comprise three consecutive glycine residues.

27. The amphiphile of claim 24 wherein A is —NR$^1$R$^2$, each of R$^1$ and R$^2$ are independently hydrocarbyl or substituted hydrocarbyl, and each of H$^1$ and H$^2$ are peptides containing 1 to 7 residues of α-amino acids selected from the group consisting of alanine, glycine, isoleucine, leucine, methionine, phenylalanine, tryptophan and valine.

28. An amphiphile selected from the group consisting of (H$_{17}$C$_8$)$_2$NCOCH$_2$OCH$_2$CO-Gly-Gly-Gly-Pro-Gly-Gly-Gly-OCH$_2$Ph (H$_{21}$C$_{10}$)$_2$NCOCH$_2$OCH$_2$CO-Gly-Gly-Gly-Pro-Gly-Gly-Gly-OCH$_2$Ph, (H$_{25}$C$_{12}$)$_2$NCOCH$_2$OCH$^2$CO-Gly-Gly-Gly-Pro-Gly-Gly-Gly-OCH$_2$Ph, (H$_{29}$C$_{14}$)$_2$NCOCH$_2$OCH$_2$CO-Gly-Gly-Gly-Pro-Gly-Gly-Gly-OCH$_2$Ph, (H$_{33}$C$_{16}$)$_2$NCOCH$_2$OCH$_2$CO-Gly-Gly-Gly-Pro-Gly-Gly-Gly-OCH$_2$Ph, (H$_{37}$C$_{18}$)$_2$NCOCH$_2$OCH$_2$CO-Gly-Gly-Gly-Pro-Gly-Gly-Gly-OCH$_2$Ph, (H$_{21}$C$_{10}$)$_2$NCOCH$_2$OCH$_2$CO-Gly-Gly-Gly-Pip-Gly-Gly-Gly-OCH$_2$Ph, (H$_{37}$C$_{18}$)$_2$NCOCH$_2$OCH$_2$CO-Gly-Gly-Gly-Pip-Gly-Gly-Gly-OCH$_2$Ph, (H$_{38}$C$_{18}$)$_2$NCOCH$_2$OCH$_2$CO-Gly-Gly-Gly-MBA-Gly-Gly-Gly-OCH$_2$Ph, (H$_{37}$C$_{18}$)$_2$NCOCH$_2$OCH$_2$CO-Gly-Gly-Gly-Leu-Gly-Gly-Gly-OCH$_2$Ph, (H$_{37}$C$_{18}$)$_2$NCOCH$_2$OCH$_2$CO-Gly-Gly-Gly-Pro-Gly-Gly-Gly-OCH$_2$CH$_3$, (H$_{37}$C$_{18}$)$_2$NCOCH$_2$OCH$_2$CO-Gly-Gly-Gly-Pro-Gly-Gly-Gly-OCH(CH$_3$)$_2$, (H$_{37}$C$_{18}$)$_2$NCOCH$_2$OCH$_2$CO-Gly-Gly-Gly-Pro-Gly-Gly-Gly-O(CH$_2$)$_8$CH$_3$, (H$_{37}$C$_{18}$)$_2$NCOCH$_2$OCH$_2$CO-Gly-Gly-Gly-Pro-Gly-Gly-Gly-OCH$_2$-o-C$_8$H$_{11}$, and (H$_{21}$C$_{10}$)N(C$_2$H$_5$)COCH$_2$OCH$_2$CO-Gly-Gly-Gly-Pro-Gly-Gly-Gly-OCH$_2$Ph.

* * * * *

UNITED STATES PATENT AND TRADEMARK OFFICE
CERTIFICATE OF CORRECTION

PATENT NO. : 7,129,208 B2 Page 1 of 1
APPLICATION NO. : 10/341960
DATED : October 31, 2006
INVENTOR(S) : Gokel et al.

It is certified that error appears in the above-identified patent and that said Letters Patent is hereby corrected as shown below:

On the Title page, and item 45

[*] Notice: Subject to any disclaimer, the term of this patent is extended or adjusted under 35 USC 154(b) by (195) days Delete the phrase "by 195" and insert -- by 208 days--

Signed and Sealed this

Ninth Day of January, 2007

JON W. DUDAS
*Director of the United States Patent and Trademark Office*